(12) United States Patent
Lee et al.

(10) Patent No.: US 9,107,816 B2
(45) Date of Patent: Aug. 18, 2015

(54) IMPLANTABLE DEVICE FOR CONTROLLED DISSOLUTION AND DIFFUSION OF LOW SOLUBILITY DRUG

(75) Inventors: Heejin Lee, Arlington, MA (US); Hong Linh Ho Duc, Watertown, MA (US); Matthew Sansone, Lowell, MA (US)

(73) Assignee: TARIS BIOMEDICAL LLC, Lexington, MA (US)

( * ) Notice: Subject to any disclaimer, the term of this patent is extended or adjusted under 35 U.S.C. 154(b) by 0 days.

(21) Appl. No.: 13/366,981

(22) Filed: Feb. 6, 2012

(65) Prior Publication Data
US 2012/0203203 A1 Aug. 9, 2012

Related U.S. Application Data

(60) Provisional application No. 61/439,665, filed on Feb. 4, 2011.

(51) Int. Cl.
| | |
|---|---|
| *A61M 31/00* | (2006.01) |
| *A61K 9/00* | (2006.01) |
| *A61K 31/337* | (2006.01) |
| *A61K 31/407* | (2006.01) |
| *A61K 31/46* | (2006.01) |
| *A61K 31/555* | (2006.01) |
| *A61K 31/7064* | (2006.01) |

(Continued)

(52) U.S. Cl.
CPC ............ *A61K 9/0024* (2013.01); *A61K 9/0034* (2013.01); *A61K 31/337* (2013.01); *A61K 31/407* (2013.01); *A61K 31/46* (2013.01); *A61K 31/555* (2013.01); *A61K 31/7064* (2013.01); *A61K 33/24* (2013.01); *A61M 31/002* (2013.01); *A61M 37/0069* (2013.01); *A61M 2210/1085* (2013.01); *A61M 2210/1089* (2013.01)

(58) Field of Classification Search
CPC . A61M 31/00; A61M 31/002; A61M 31/007; A61M 2210/1085; A61M 2210/1089; A61M 37/0069; A61M 25/0041; A61M 27/008; A61K 9/0024; A61K 9/0034; A61K 9/0036; A61K 9/0039
USPC ............ 604/890.1, 891.1, 6.16, 93.01, 95.03, 604/95.04, 197, 517, 544; 424/426
See application file for complete search history.

(56) References Cited

U.S. PATENT DOCUMENTS

| | | |
|---|---|---|
| 3,854,480 A | 12/1974 | Zaffaroni |
| 3,888,975 A | 6/1975 | Ramwell |
| 3,901,232 A | 8/1975 | Michaels et al. |

(Continued)

FOREIGN PATENT DOCUMENTS

| | | |
|---|---|---|
| DE | 3332156 A1 | 3/1985 |
| EP | 0572932 A2 | 12/1993 |

(Continued)

*Primary Examiner* — Quynh-Nhu H Vu
(74) *Attorney, Agent, or Firm* — Sutherland Asbill & Brennan LLP

(57) ABSTRACT

Implantable drug delivery devices are provided that are deformable between a relatively straightened shape suitable for deployment and a retention shape suited to retain the device within the bladder or other body cavity. While in the body cavity, the devices release drug from solid drug units housed in the devices. The devices are designed to house the solid drug units in a way that exposes one or more sides of the solid drug units to the fluid at the in vivo site of deployment. Methods for using the devices for administering drug and making the devices also are provided.

18 Claims, 15 Drawing Sheets

(51) Int. Cl.
*A61K 33/24* (2006.01)
*A61M 37/00* (2006.01)

(56) References Cited

U.S. PATENT DOCUMENTS

| | | | |
|---|---|---|---|
| 3,935,860 A | 2/1976 | Hoff | |
| 4,016,251 A | 4/1977 | Higuchi et al. | |
| 4,235,236 A | 11/1980 | Theeuwes | |
| 4,392,848 A | 7/1983 | Lucas et al. | |
| 4,449,980 A | 5/1984 | Millar et al. | |
| 4,475,916 A | 10/1984 | Himmelstein | |
| 4,629,449 A | 12/1986 | Wong | |
| 4,655,219 A | 4/1987 | Petruzzi | |
| 4,678,463 A | 7/1987 | Millar | |
| 4,871,542 A | 10/1989 | Vilhardt | |
| 4,968,507 A | 11/1990 | Zentner et al. | |
| 5,366,738 A | 11/1994 | Rork et al. | |
| 5,441,550 A | 8/1995 | Hassenboehler, Jr. et al. | |
| 5,499,997 A | 3/1996 | Sharpe et al. | |
| 5,516,522 A | 5/1996 | Peyman et al. | |
| 5,551,954 A | 9/1996 | Buscemi et al. | |
| 5,709,874 A | 1/1998 | Hanson et al. | |
| 5,756,127 A * | 5/1998 | Grisoni et al. | 424/489 |
| 5,788,980 A | 8/1998 | Nabahi | |
| 5,795,591 A | 8/1998 | Lee et al. | |
| 5,797,898 A | 8/1998 | Santini, Jr. et al. | |
| 5,830,230 A | 11/1998 | Berryman et al. | |
| 5,851,217 A | 12/1998 | Wolff et al. | |
| 5,855,906 A | 1/1999 | McClay | |
| 5,869,081 A | 2/1999 | Jackanicz et al. | |
| 5,972,372 A * | 10/1999 | Saleh et al. | 424/432 |
| 5,989,581 A * | 11/1999 | Groenewegen | 424/433 |
| 6,039,968 A | 3/2000 | Nabahi | |
| 6,083,933 A | 7/2000 | Hahn | |
| 6,086,909 A | 7/2000 | Harrison et al. | |
| 6,139,535 A | 10/2000 | Greelis et al. | |
| 6,171,298 B1 | 1/2001 | Matsuura et al. | |
| 6,183,461 B1 | 2/2001 | Matsuura et al. | |
| 6,207,180 B1 | 3/2001 | Ottoboni et al. | |
| 6,293,923 B1 | 9/2001 | Yachia et al. | |
| 6,398,718 B1 | 6/2002 | Yachia et al. | |
| 6,413,540 B1 * | 7/2002 | Yaacobi | 424/427 |
| 6,416,780 B1 | 7/2002 | Passmore et al. | |
| 6,444,224 B1 | 9/2002 | Rathbone et al. | |
| 6,464,999 B1 | 10/2002 | Huo et al. | |
| 6,482,837 B1 | 11/2002 | Wood | |
| 6,491,666 B1 * | 12/2002 | Santini et al. | 604/191 |
| 6,682,473 B1 | 1/2004 | Matsuura et al. | |
| 6,712,784 B2 | 3/2004 | Huang | |
| 6,746,421 B2 | 6/2004 | Yachia et al. | |
| 6,749,617 B1 | 6/2004 | Palasis et al. | |
| 6,753,011 B2 | 6/2004 | Faour | |
| 6,808,522 B2 | 10/2004 | Richards et al. | |
| 6,899,890 B2 | 5/2005 | Kirschner et al. | |
| 6,932,810 B2 | 8/2005 | Ryan | |
| 6,951,654 B2 | 10/2005 | Malcolm et al. | |
| 6,976,950 B2 | 12/2005 | Connors et al. | |
| 6,988,983 B2 | 1/2006 | Connors et al. | |
| 7,005,138 B2 | 2/2006 | Mahashabde et al. | |
| 7,074,178 B2 | 7/2006 | Connors et al. | |
| 7,521,064 B2 | 4/2009 | Saxena et al. | |
| 7,647,112 B2 | 1/2010 | Tracey et al. | |
| 7,862,552 B2 | 1/2011 | McIntyre et al. | |
| 7,993,411 B2 * | 8/2011 | Kennedy et al. | 623/23.7 |
| 8,521,273 B2 * | 8/2013 | Kliman | 604/20 |
| 2003/0059456 A1 | 3/2003 | Malcolm et al. | |
| 2003/0118649 A1 | 6/2003 | Gao et al. | |
| 2003/0118692 A1 | 6/2003 | Wang et al. | |
| 2003/0139800 A1 | 7/2003 | Campbell | |
| 2004/0011693 A1 * | 1/2004 | Prenger et al. | 206/531 |
| 2004/0022824 A1 * | 2/2004 | Li et al. | 424/423 |
| 2004/0220552 A1 | 11/2004 | Heruth et al. | |
| 2004/0260272 A1 | 12/2004 | Friedman et al. | |
| 2005/0234013 A1 | 10/2005 | Parsons | |
| 2005/0234431 A1 | 10/2005 | Williams et al. | |
| 2005/0238733 A1 | 10/2005 | Henry | |
| 2006/0105010 A1 | 5/2006 | Rahe et al. | |
| 2006/0134176 A1 * | 6/2006 | Bartels | 424/427 |
| 2006/0195187 A1 * | 8/2006 | Stegmann et al. | 623/4.1 |
| 2006/0234978 A1 | 10/2006 | Marcum | |
| 2007/0172507 A1 | 7/2007 | Zupkas et al. | |
| 2007/0172508 A1 | 7/2007 | Zupkas et al. | |
| 2007/0202151 A1 | 8/2007 | Lee et al. | |
| 2007/0254014 A1 | 11/2007 | Ahmed et al. | |
| 2008/0051740 A1 | 2/2008 | Sokal et al. | |
| 2008/0188836 A1 * | 8/2008 | Weber et al. | 604/890.1 |
| 2008/0221557 A1 * | 9/2008 | Santini et al. | 604/891.1 |
| 2008/0243056 A1 * | 10/2008 | Hillis et al. | 604/66 |
| 2008/0302695 A1 * | 12/2008 | Meeren et al. | 206/531 |
| 2009/0149833 A1 * | 6/2009 | Cima et al. | 604/517 |
| 2010/0003297 A1 | 1/2010 | Tobias et al. | |
| 2010/0330149 A1 | 12/2010 | Daniel et al. | |
| 2010/0331770 A1 * | 12/2010 | Lee et al. | 604/57 |
| 2011/0060309 A1 * | 3/2011 | Lee et al. | 604/500 |
| 2011/0112475 A1 | 5/2011 | Benson | |
| 2011/0137244 A1 | 6/2011 | Lee et al. | |
| 2011/0152839 A1 | 6/2011 | Cima et al. | |
| 2012/0089121 A1 | 4/2012 | Lee et al. | |
| 2012/0089122 A1 | 4/2012 | Lee et al. | |

FOREIGN PATENT DOCUMENTS

| | | |
|---|---|---|
| WO | 991884 A1 | 4/1999 |
| WO | 03009882 A2 | 2/2003 |
| WO | 2005115245 A1 | 12/2005 |
| WO | 2007115259 A2 | 10/2007 |
| WO | 2012018923 A1 | 2/2012 |
| WO | 2012019155 A1 | 2/2012 |

* cited by examiner

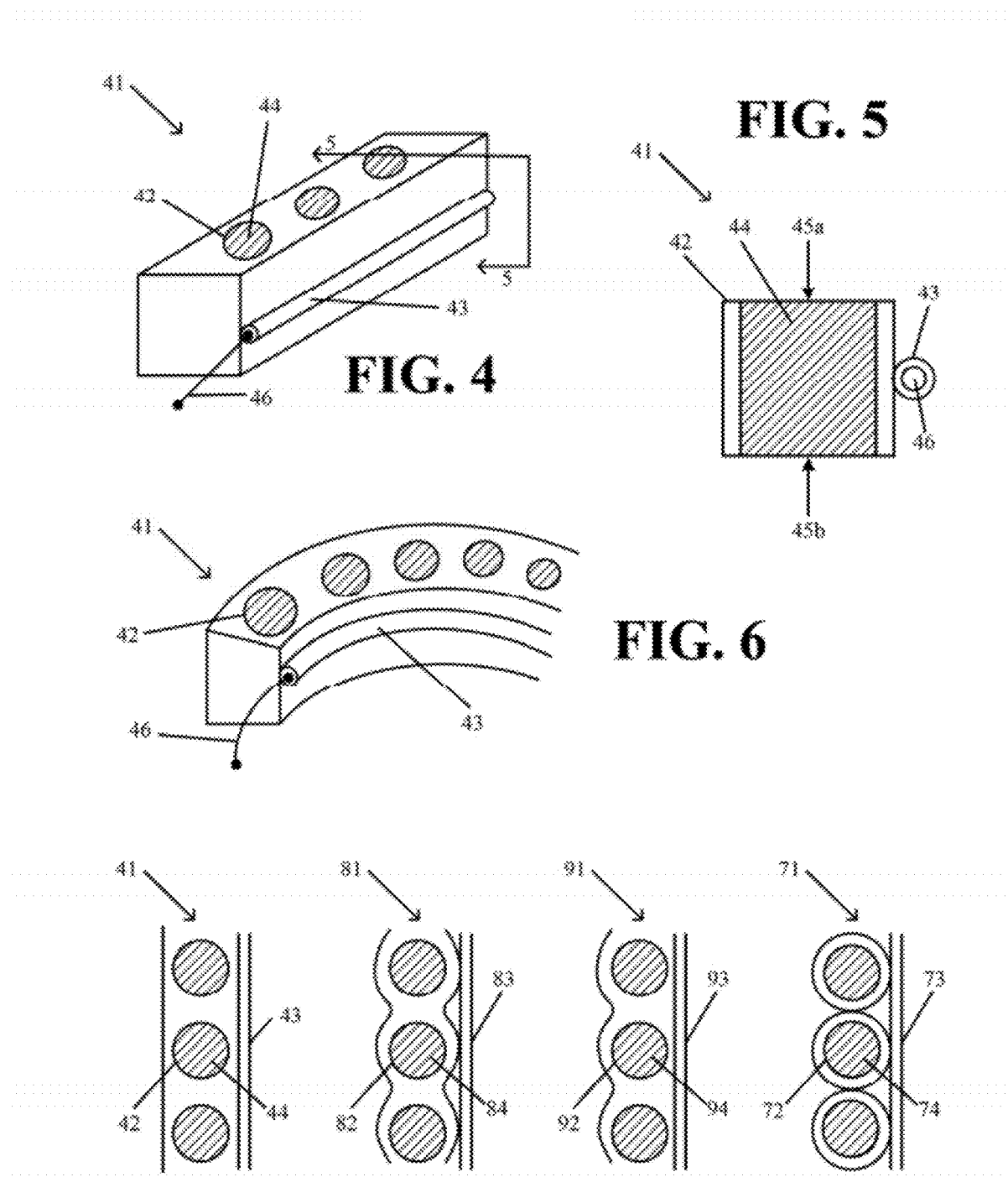

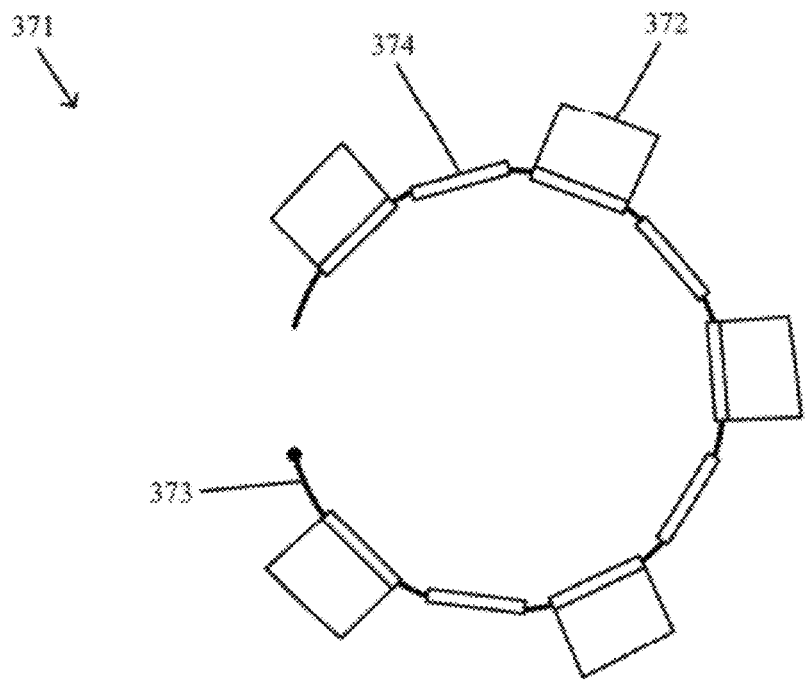
FIG. 37
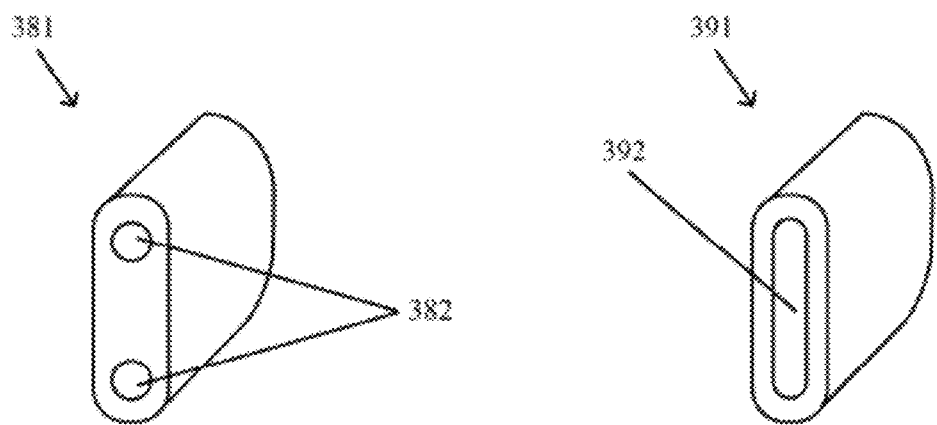
FIG. 38  FIG. 39

IMPLANTABLE DEVICE FOR CONTROLLED DISSOLUTION AND DIFFUSION OF LOW SOLUBILITY DRUG

CROSS-REFERENCE TO RELATED APPLICATION

This application claims priority to U.S. Provisional Patent Application No. 61/439,665, filed Feb. 4, 2011, which is incorporated herein by reference.

BACKGROUND

Systemic methods of drug delivery may produce undesirable side effects and may result in the distribution and metabolization of the drug by physiological processes, ultimately reducing the quantity of drug to reach the desired site. A variety of devices and methods have been developed to deliver drug in a more targeted manner, e.g., locally or regionally, which may address many of the problems associated with systemic drug delivery. Local delivery of drug to some tissue sites, however, has room for improvement, particularly with respect to extended drug delivery with minimally invasive devices and methods with minimum patient discomfort from the presence of the device itself.

For example, interstitial cystitis (IC) is a urological condition characterized by pain, increased urinary frequency, and urgency. This condition may also involve varying degrees of urinary incontinence and sexual dysfunction. IC and Painful Bladder Syndrome include patients with urinary pain not attributable to other causes, such as infection or urinary stones, and are estimated to affect approximately 3 to 8 million people in the U.S. alone, the majority of whom are women. Berry, et al., *J. Urol.* 186(2):540-44 (2011). IC is a serious condition with unmet medical needs. Other therapies also could benefit from improved intravesical drug delivery devices, particularly where local delivery of a drug to the bladder is preferred or necessary—such as when the side effects associated with systemic delivery of the drug are intolerable and/or when bioavailability from oral administration is too low.

A need exists for an intravesical drug delivery device that is sufficiently small to avoid unnecessary discomfort and pain during and following deployment of the device into patients, that can reduce the number of surgical or interventional procedures required for implantation and delivery of drug over the treatment period—e.g., that provides controlled delivery over an extended period, and that can carry an effective amount of drug for the extended period in a sufficiently small payload volume. In bladder applications, the device desirably should be retained in the bladder and not be excreted before the drug payload can be at least substantially released, even when the drug needs to be delivered over a period of several days or weeks.

Currently, conventional bladder treatments include (1) delivery via instillation, which must be repeated, (2) delivery via conventional devices, which must be re-filled once implanted; (3) delivery via catheters, which provide a path for bacteria to migrate into the bladder, and (4) systemic delivery, which increases the risk of side effects and reduced drug exposure to the target site. In general, better devices are needed for controlled delivery of drug to the bladder. Desirably, the implantable device should be easy to deliver into (and if necessary, remove from) the bladder with reduced pain or discomfort to the patient.

PCT Application Publications WO 2010/151893 and WO 2010/151896 by Taris Biomedical Inc. describe drug delivery devices that provide controlled release of drug from a housing. The device may be free floating in a patient's bladder, yet tolerably and wholly retained in the patient's bladder while locally releasing the drug over an extended period.

It would be desirable, however, to provide new designs of intravesical drug delivery devices, and other implantable devices capable of delivering drugs at effective release rates for a range of different drugs, including those with relatively low aqueous solubility.

SUMMARY

In one aspect, drug delivery devices are provided that include a drug housing portion which comprises at least one solid drug unit including a drug, and at least one housing encasing a first portion of the surface of the at least one solid drug unit, and having at least one defined opening that exposes a second portion of the surface of the at least one solid drug unit. Release of the drug from the device is controlled by erosion of the exposed second portion of the surface of the at least one solid drug unit, and the device is elastically deformable between a relatively straightened shape suited for insertion through a lumen into a body cavity of a patient and a retention shape suited to retain the device within the body cavity. The rate of drug release from the drug delivery device may be directly proportional to and limited by the total exposed surface area of the solid drug units. Drug release may be substantially zero order over an extended period, such as from one day to one month.

In another aspect, implantable drug delivery devices are provided that comprise a drug housing portion, which comprises at least two solid drug units, and at least one housing. The at least one housing encases a first portion of the surface of each solid drug unit, and has at least two defined openings that expose a second portion of the surface of each solid drug unit. The drug delivery device is elastically deformable between a relatively straightened shape suited for insertion through a lumen into a body cavity of a patient and a retention shape suited to retain the device within the body cavity. In certain embodiments, the at least one housing comprises at least three defined openings so that a third portion of the surface of at least one solid drug unit is exposed. In particular embodiments, the at least one housing comprises at least four defined openings so that a third portion of the surface of each solid drug unit is exposed.

In a further aspect, a drug delivery device is provided which is insertable into the bladder of a patient and comprises a retention frame comprising an elastic wire having a coiled shape; a plurality of solid drug tablets, each having a peripheral surface between opposed end faces; and a plurality of modular housing units attached to the retention frame and securing the plurality of solid drug tablets, wherein each modular housing unit holds one of the solid drug tablets about its peripheral surface and has one or two openings exposing, respectively, one or both end faces of said drug tablet.

In another aspect, a drug delivery device is provided which is insertable into the bladder of a patient and which includes a housing which comprises a flexible elongated monolithic structure having a longitudinal axis and a plurality of separate drug reservoir lumens oriented substantially perpendicularly to the longitudinal axis; and a plurality of solid drug tablets disposed in the plurality of separate drug reservoir lumens.

In still another aspect, methods are provided for locally administering a drug to a patient. The method may include providing a drug delivery device which comprises two or more solid drug units secured in at least one housing encasing a first portion of the surface of each solid drug unit and having at least one defined opening that exposes a second portion of the surface of each solid drug unit, the device being elastically deformable between a relatively straightened shape suited for insertion through a patient's urethra and a retention shape suited to retain the drug delivery device within the patient's bladder; inserting the drug delivery device in the relatively straightened shape through the patient's urethra and into the patient's bladder; permitting fluid in the patient's bladder to contact the second portion of the surface of each solid drug unit; and dissolving drug, from the second portion of the surface of each solid drug unit drug, into the fluid in contact with said second portion, thereby releasing the drug into the bladder.

BRIEF DESCRIPTION OF THE DRAWINGS

FIG. 4 is a depiction of one embodiment of a monolithic housing having a continuous structure with multiple drug reservoir lumens, wherein the device is held in a relatively straightened shape.

FIG. 5 is a cross-sectional view of one embodiment of a monolithic housing having cylindrical drug reservoir lumens with two defined openings.

FIG. 6 is a depiction of a portion of one embodiment of a drug delivery device that is in a retention shape.

FIG. 7 is a depiction of a top view of a portion of one embodiment of a drug delivery device having a monolithic structure.

FIG. 8 is a depiction of a top view of a portion of one embodiment of a drug delivery device in which a portion of the housing roughly conforms to the shape of a series of drug reservoir lumens.

FIG. 9 is a depiction of a top view of a portion of one embodiment of a drug delivery device in which one side of the device has walls that conform to the shape of a series of drug reservoir lumens.

FIG. 10 is a depiction of a top view of a portion of one embodiment of a drug delivery device in which the drug reservoir lumens have circular walls.

FIG. 37 is a depiction of a embodiment of a device having modular housing units connected by a retention frame and separated by spacers.

FIG. 38 is a depiction of one embodiment of a spacer with two retention frame lumens.

FIG. 39 is a depiction of one embodiment of a spacer with one retention frame lumen.

DETAILED DESCRIPTION

Figure 1:
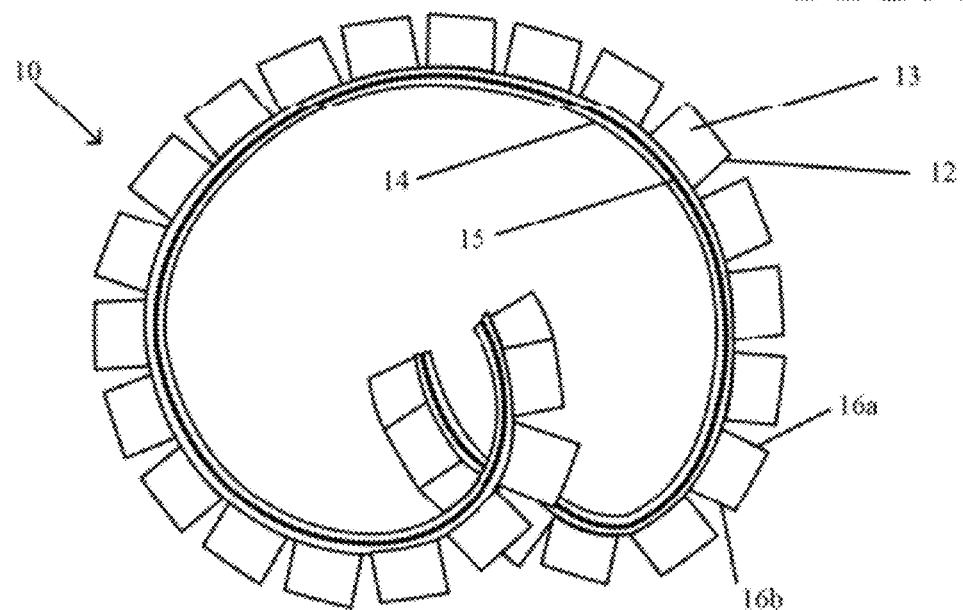
FIG. 1 is a depiction of one embodiment of a drug delivery device having a monolithic drug housing in a retention shape.

Implantable devices and methods are provided herein for administering a drug from a device deployed through a lumen into a body cavity of a patient, such as the bladder. Advantageously, the present devices enable low solubility drugs to be released at therapeutically effective, controlled rates over an extended period. Importantly, the devices provide sufficient direct contact between solid drug units and with a biological fluid surrounding the device when deployed in vivo, while being retained in a body cavity. In embodiments, release of the drug from the device is controlled by erosion of an exposed portion of the surface of a solid drug unit, such that the rate of drug release from the drug delivery device may be directly proportional to and limited by the total exposed surface area of the solid drug units.

The devices can be elastically deformable between a relatively straightened shape suited for insertion through a lumen into a body cavity of a patient and a retention shape suited to retain the device within the body cavity. When in the retention shape after deployment in the bladder, for example, the devices may resist excretion in response to the forces of urination or other forces. Since the devices are designed to be retained within a lumen or body cavity, they are capable of overcoming some of the deficiencies of conventional treatments, such as those related to the bladder. The devices described herein can be inserted once and release drug over a desired period of time without surgery or frequent interventions. The devices, as a result, may reduce the opportunity for infection and side effects, increase the amount of drug delivered locally or regionally to the bladder, or improve the quality of life of the patient during the treatment process. After drug release, the devices can be removed or be bioerodible, at least in part, to avoid a retrieval procedure.

The device may be loaded with at least one drug in the form of solid drug units, such as tablets, capsules, or pellets. Providing one or more drugs in solid form to a patient is often advantageous. Solid drugs can provide a relatively large drug payload volume to total device volume and potentially enhance stability of the drugs during shipping, storage, before use, or before drug release. Solid drugs, however, should be solubilized in vivo in order to diffuse into a patient's tissues, and the rate of that solubilization should be sufficient to provide a therapeutically effective amount of drug. One or both of these objectives, along with others, may be achieved when the devices described herein are used to deliver one or more drugs, particularly if the drugs have low aqueous solubility.

The devices and methods disclosed herein build upon those described in U.S. Application Publication No. 2007/0202151 (MIT 11824); U.S. Application Publication No. 2009/0149833 (MIT 12988); U.S. Application Publication No. 2010/0003297 (MIT 12805); U.S. Application Publication No. 2010/0331770 (TB 101); U.S. Application Publication No. 2010/0330149 (TB 102); U.S. Application Publication No. 2010/0060309 (TB 108); U.S. Application Publication No. 2011/0202036 (TB 107); U.S. Application Publication No. 2011/0152839 (TB 112); U.S. Application Publication No. 2011/0218488 (TB 103); PCT/US11/46843, filed Aug. 5, 2011 (TB 113); U.S. Application No. 13/267,560, filed Oct. 6, 2011 (TB 116); U.S. Application No. 13/267,469, filed Oct. 6, 2011 (TB 117); and U.S. Application No. 13/347,513, filed Jan. 10, 2012 (TB 120), each of which is incorporated by reference herein.

I. The Implantable Drug Delivery Device

Generally, the implantable drug delivery devices include a drug housing portion which comprises at least one solid drug unit including a drug, and at least one housing encasing a first portion of the surface of the at least one solid drug unit, and having at least one defined opening that exposes a second portion of the surface of the at least one solid drug unit. Release of the drug from the device is controlled by erosion of the exposed second portion of the surface of the at least one solid drug unit, and the device is elastically deformable between a relatively straightened shape suited for insertion through a lumen into a body cavity of a patient and a retention shape suited to retain the device within the body cavity. The rate of drug release from the drug delivery device may be directly proportional to and limited by the total exposed surface area of the solid drug units. In such an embodiment, drug release in vivo may be substantially zero order over an extended period, such as from one day to one month.

In one embodiment, the drug housing portion may include at least two solid drug units and at least one housing. The at least one housing encases a first portion of the surface of each solid drug unit. At least one other portion of each of the solid drug units may be exposed. As used herein with regard to the at least two solid drug units, an "exposed" portion of a solid drug unit is one that, due to a defined opening on the housing, is capable of directly contacting a fluid, including a biological fluid, in the body lumen or cavity after deployment of the device. In one embodiment, the biological fluid is urine and the body lumen or cavity comprises the bladder.

In some embodiments, the at least one housing comprises at least two defined openings so that a second portion of the surface of each of the at least two solid drug units is exposed.

In some embodiments, the at least one housing comprises at least three defined openings so that a third portion of the surface of at least one of the at least two solid drug units is exposed.

In some embodiments, the at least one housing comprises at least four defined openings so that a third portion of each of the at least two drug units is exposed.

As used herein with regard to the at least one housing, the term "defined opening" refers to any orifice in the at least one housing that exposes one portion of the surface of a drug unit. Each defined opening may be any suitable shape, such as polygonal, circular, elliptical, or non-circular. The size of each defined opening is limited only by the size of the device and the desired surface area of each solid drug unit that is exposed. Certain embodiments of the device expose a total surface area of at least one solid drug unit that remains substantially constant over all or a substantial portion of the drug release period, which may beneficially provide a relatively constant rate of drug release.

Generally, the devices are elastically deformable between a relatively straightened shape suited for insertion through a lumen (such as the urethra) into a body cavity (such as the bladder) of a patient and a retention shape suited to retain the device within the body cavity. In some embodiments, the material used to form the at least one housing is capable of forming the retention shape without a retention frame. In other embodiments, the material used to form the at least one housing is associated with a retention frame.

The material used to form the at least one housing may be elastic or flexible to permit moving the device between the relatively straightened shape and the retention shape. The material used to form the at least one housing also may be water permeable, porous, or both. A porous material may be drug permeable, depending on the particular drug used. The material used to form the at least one housing may be one or more polymeric materials, biocompatible elastomeric materials, or a combination thereof. In one embodiment, the at least one housing is formed of silicone.

Generally, the at least one housing may have a monolithic or modular structure. The monolithic housings are continuous structures that house the at least two solid drug units, and may or may not include a retention frame. As used herein, a "continuous structure" is one in which the two or more drug-encasing portions of the housing are held in contact with each other by the material or materials from which the housing is made, not a retention frame. A retention frame, however, may be included in the devices having a continuous, i.e., monolithic, structure. A "continuous structure," in certain embodiments, may include two or more different flexible materials that have been affixed to each other to form the housing, or it may include a single material that is shaped to form the housing. The modular housings are typically formed from at least two separate housing units, each encasing at least one solid drug unit. In some embodiments, the at least two separate modular housing units are connected via a retention frame.

Monolithic Housings

In certain embodiments, the monolithic housings comprise a continuous material that defines one or more drug reservoir lumens, which are designed to encase the drug units. In other embodiments, the monolithic housings comprise a continuous material that defines one or more drug reservoir lumens, which are designed to encase the drug units, and a retention frame. The continuous material may or may not include one or more retention frame lumens, which house a retention frame. In certain embodiments, the drug reservoir lumens and the retention frame lumen(s) are discrete from each other, although other configurations are possible. In particular embodiments, the retention frame lumen(s) is oriented parallel to the longitudinal axis of the housing, although other alignments are possible.

In certain embodiments, the housings comprise a flexible elongated monolithic structure having a longitudinal axis and a plurality of separate drug reservoir lumens oriented parallel to the longitudinal axis.

Figure 2:
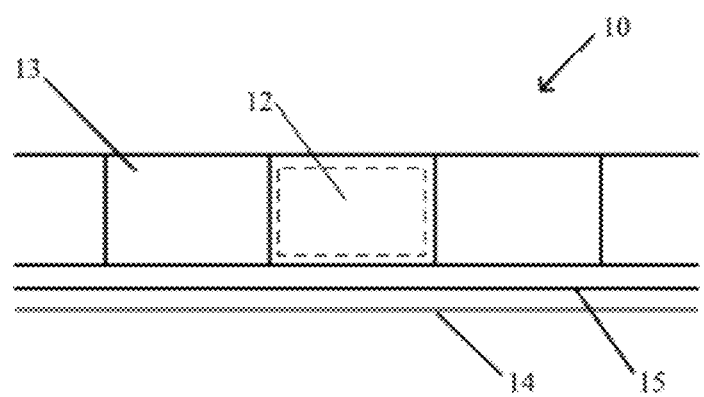
FIG. 2 is a depiction of a portion of one embodiment of a drug delivery device having a monolithic housing that is held in a relatively straightened shape.
Figure 3:
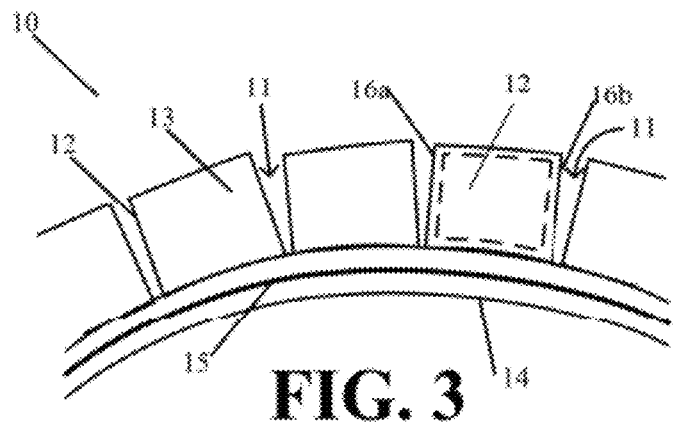
FIG. 3 is a depiction of a portion of one embodiment of a drug delivery device having a monolithic housing that is in a retention shape.

FIGS. 1-3 depict one embodiment of a drug delivery device 10 having a monolithic drug housing. The housing, in this embodiment, includes an elongated silicone tube and comprises a plurality of solid drug units 12 (twenty-seven in this embodiment), each being disposed within separate portions 13 of the at least one housing, each separate portion having two defined openings 16a and 16b. The defined openings may be formed by cutting interfaces of the adjacent portions that house the solid drug units. Solid drug unit 12 may be a drug tablet or capsule. The adjacent portions 13, which may be called "drug reservoir lumens," are, in this embodiment, silicone tube segments that are connected together via at least one secondary tube 14. The secondary tube's lumen is a retention frame lumen. Within the retention frame lumen, is a retention frame 15. In other embodiments, the housing is in a form other than a tube.

The device shown in FIG. 1 can flex between a relatively straightened shape suited for insertion through a lumen into a body cavity of a patient (FIG. 2) and a retention shape suited to retain the device within the body cavity (FIGS. 1 and 3). FIGS. 2 and 3 are close up views of a portion of the device shown in FIG. 1. As shown in FIGS. 1 and 3, in the retention shape, open gaps 11 are provided between the separate portions 13 of the at least one housing. This allows the solid drug units' surfaces at the gap to be exposed to the fluid at the in vivo deployment site. In this embodiment, dissolution and release of drug from each drug unit 12 occurs from two opposed sides of the drug unit. The area of the two open sides of the housing unit, in this embodiment, controls the drug release from each drug unit.

In embodiments that include a retention frame, the retention frame, when the device is in the retention shape, may have any orientation with reference to the monolithic housings or modular housing units described herein, lying either inside, outside, above, or below the housing or moving with reference to the housing as the device moves through the lumen and in the body cavity in which it is deployed. For example, the device shown in FIG. 1 includes a retention frame 15 that lies inside the perimeter of the device's housing. In other embodiments, the device includes a retention frame that lies below the housing (such that the retention frame would not be visible in FIG. 1).

A particular orientation between the housing and retention frame can be maintained by filling the retention frame lumen with a filling material, such as a silicone adhesive, after the retention frame is loaded into the retention frame lumen. The filling material may cure or solidify to prevent movement of one portion with reference to the other. Other means of maintaining the orientation of the retention frame with reference to the housing also can be used.

In the embodiment shown in FIG. 1, the drug reservoir lumens 13 may have an inner diameter of about 1:3 to about 3.3 mm, such as about 1.5 to about 3.1 mm, an outer diameter of about 1.7 to about 3.7 mm, such as about 1.9 to about 3.4 mm, and the housing may have a length of about 12 to 21 cm, such as about 14 to 16 cm.

In the embodiment shown in FIG. 1 and other embodiments described herein, each drug reservoir lumen may hold one or several drug tablets or other solid drug units. In one embodiment, the device holds from about 10 to 100 cylindrical drug tablets, such as mini-tablets, among a number of discrete drug reservoir lumens. In certain embodiments, the mini-tablets may each have a diameter of about 1.0 to about 3.3 mm, such as about 1.5 to about 3.1 mm, and a length of about 1.5 to about 4.7 mm, such as about 2.0 to about 4.5 mm.

In certain embodiments, the housings comprise a flexible elongated monolithic structure having a longitudinal axis and a plurality of separate drug reservoir lumens oriented perpendicular to the longitudinal axis.

FIGS. 4 and 5 show one embodiment of a monolithic housing 41 having a single, continuous structure with multiple, discrete drug reservoir lumens 42 and having at least one retention frame lumen 43 in which a retention frame 46 is disposed. Each drug reservoir lumen 42 has two defined openings, as shown in FIG. 5, and is dimensioned to hold at least one solid drug unit 44. Solid drug unit 44 may be a drug tablet or capsule. In other embodiments not shown, each drug reservoir lumen has one defined opening. The overall shape of the housing 41 may be formed by a molding process, or by a combination of an extrusion process to form rods, strips, or sheets, which subsequently may be cut. The drug reservoir lumens 42 may be created by a molding process or by a mechanical punching or drilling process. The housing may be formed of a flexible polymer, such as silicone.

FIG. 5 is a cross-sectional view of the plane that bisects one of the drug reservoir lumens 42 of the housing shown in FIG. 4 along line 5-5. As shown in FIG. 5, the monolithic housing 41 has two defined openings (45a, 45b) in its drug reservoir lumen 42 that expose both flat ends of the solid drug unit 44. The retention frame lumen 43, in this embodiment, is aligned parallel to the longitudinal axis of the housing and perpendicular to the drug reservoir lumen 42.

FIG. 6 is a perspective view of a portion of the embodiment of the device 41 shown in FIG. 4 when the device is in its retention shape, which is taken when the retention frame 46 is disposed in the retention frame lumen 43. The drug reservoir lumens 42 and the retention frame 46 in the monolithic housing of this embodiment are oriented so that the drug reservoir lumens 42 are outside the retention frame's 46 arc. The housing in FIG. 6 can be rotated 180 degrees about the retention frame 46 to yield a configuration in which the drug reservoir lumens 42 are arranged within the retention frame's 46 arc.

In embodiments of the devices that include a retention frame, the housings may terminate at the end of the retention frame, the retention frame may extend beyond the housings, or a combination thereof.

In the embodiments that include a retention frame, the housing—which may or may not have a retention frame lumen—and the retention frame are associated with each other to form part of the drug delivery device. A variety of different associations are envisioned. For example, the longitudinal axis of the housing and the retention frame may be at least partially aligned. In other words, the housing may extend along a portion or the entire length of the retention frame, substantially parallel or coincident with the retention frame.

In other embodiments, the housing may be attached to only a portion of the retention frame. The housing may have first and second portions—such as first and second end portions—that are attached to a portion or portions of the retention frame. For example, the housing may include discrete retention frame lumens at the first and second end portions through which the retention frame is threaded; or the housing may be bereft of retention frame lumens so the retention frame is continuously or intermittently attached to the housing by other suitable means, such as an adhesive.

In other embodiments, the portion of the housing that encases the solid drug units may be continually or intermittently connected to a retention frame lumen, which may extend along a portion or the entire length of the housing. In some embodiments, the retention frame lumen may extend beyond the portion of the housing that encases the solid drug units.

FIG. 7 is a top view of the portion of the housing 41 shown in FIGS. 4 and 5. In the embodiment shown in FIG. 7, the retention frame lumen 43 and portion of the housing containing the drug reservoir lumens 42, which house the solid drug units 44, are connected along their entire lengths. Other embodiments, however, are envisioned, such as those shown in FIGS. 8-10. FIGS. 8-10 depict possible alternative designs for the housing shown in FIG. 7.

FIG. 8 depicts a portion of an embodiment of a monolithic housing 81 in which the portion of the housing containing the drug reservoir lumens 82 has walls that roughly conform to the shape of the drug reservoir lumens 82 which house the solid drug units 84. As a result, the portion of the housing containing the drug reservoir lumens 82 in FIG. 8 is only intermittently connected to the retention frame lumen 83.

FIG. 9 depicts a portion of an embodiment of a monolithic housing 91 in which the portion of the housing containing the drug reservoir lumens 92 has walls that conform to the shape of the drug reservoir lumens 92 on the side that is opposite the retention frame lumen 93. The retention frame lumen 93 is attached along the entire length of the portion of the housing that contains the drug reservoir lumens 92, which house the solid drug units 94.

FIG. 10 depicts a portion of a monolithic housing 71 in which the circular walls that form the drug reservoir lumens 72 are connected to the retention frame lumen 73. In one embodiment of the monolithic housing of FIG. 10, the walls that form one drug reservoir lumen 72 are connected to the walls that form the adjacent drug reservoir lumens 72, which house the solid drug units 74. In another embodiment of the monolithic housing of FIG. 10, the walls that form one drug reservoir lumen 72 are not connected to the walls that form the adjacent drug reservoir lumens. This embodiment may be formed by separately forming the drug reservoir lumens and attaching them to the retention frame lumen, and, if desired, attaching to each other the walls of adjacent drug reservoir lumens. The drug reservoir lumens may be placed on the retention frame lumen so that they are adjacent to each other or they may be spaced apart from each other at any desired interval.

The designs of the housings shown in FIGS. 8-10 and other embodiments described herein may be employed to reduce the total volume of the wall material defining the drug reservoir lumens, thereby possibly increasing the housing's flexibility, compressibility, or both. Moreover, the designs of FIGS. 7-10, in other embodiments, do not include a retention frame lumen.

For all embodiments described herein, including those with modular housings, the solid drug units may completely or substantially fill the drug reservoir lumens. In one embodiment, any space in the drug reservoir lumen that does not contain the drug may be filled with a filling material. This may be done for the purpose of controlling the surface area of drug unit exposed to biological fluid in vivo, and/or for the purpose of adding volume to the overall device where drug payload is not needed but overall device volume is needed, for example, for purposes of enabling or enhancing retention of the device in vivo. The filling material may be a polymeric material. The polymeric material may be placed in the drug reservoir lumen in workable form and may cure therein. Suitable polymeric materials may cure at room temperature or in response to an external stimulus, such as heat. The filling material may be a buoyancy-enhancing material, such as a closed-cell foam or gas-generating and/or -containing component.

In embodiments in which they exist, the gaps between solid drug units may serve as reliefs that accommodate deformation or movement of the device, while permitting the individual drug units to retain their solid form during storage and deployment. Thus, the drug delivery device may be relatively flexible or deformable despite being loaded with a solid drug, as each drug unit may be permitted to move with reference to adjacent drug units. Along the length of the device, the drug units may have the same composition or may vary in composition.

For all embodiments described herein, including those with modular housings, the solid drug units may be retained in the drug reservoir lumens of the housings by frictional engagement, adhesive, tabs or other mechanical locking feature, or a combination thereof. For example, if the drug reservoir lumen has only one defined opening—i.e., one closed end—then an adhesive may be applied to any of the walls of the drug reservoir lumen—such as the inner surface of the wall distal to the drug reservoir lumen—before inserting the solid drug unit into the drug reservoir lumen. As another example, if the drug reservoir lumen has two defined openings—i.e. open at both ends—then the drug reservoir lumen may be formed in a way that increases the friction between the drug reservoir lumen's walls and the solid drug unit; adhesive may or may not be used.

Generally, the walls defining the drug reservoir lumens can be of any shape capable of encasing a solid drug unit. In certain embodiments, the walls defining the drug reservoir lumens can be straight, concave, or convex when viewed in cross-section; and the thicknesses of the walls may vary.

Figure 11:
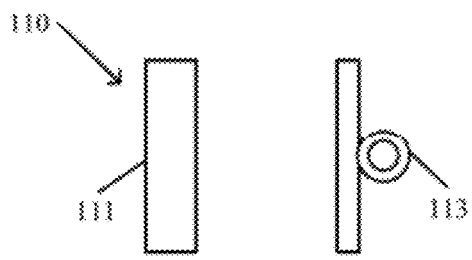
FIG. 11 is a cross-sectional view of one embodiment of a drug reservoir lumen having walls of different thickness and two defined openings.
Figure 15:
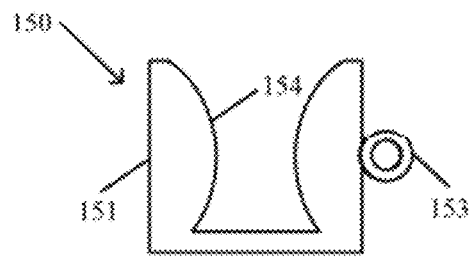
FIG. 15 is a cross-sectional view of one embodiment of a drug reservoir lumen having convex walls and one defined opening.
Figure 12:
FIG. 12 is a cross-sectional view of one embodiment of a drug reservoir lumen having convex walls and two defined openings.
Figure 16:
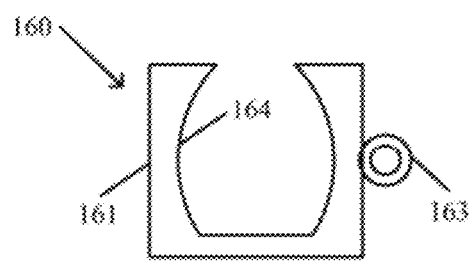
FIG. 16 is a cross-sectional view of one embodiment of a drug reservoir lumen having concave walls and one defined opening.
Figure 13:
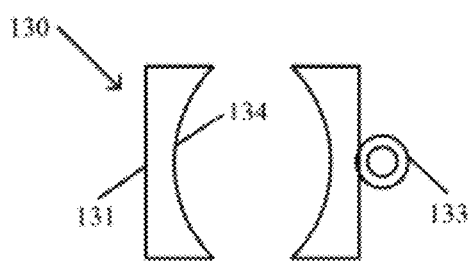
FIG. 13 is a cross-sectional view of one embodiment of a drug reservoir lumen having concave walls and two defined openings.
Figure 14:
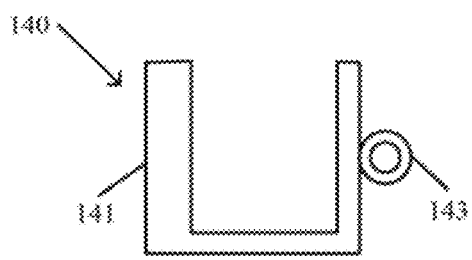
FIG. 14 is a cross-sectional view of one embodiment of a drug reservoir lumen having walls of different thickness and one defined opening.

Like FIG. 5, FIGS. 11-16 are cross-sectional views of a plane that bisects a drug reservoir lumen of a device similar to FIG. 4. Whereas FIG. 5 depicts a cross-sectional view of the cylindrical drug reservoir lumen 42 of FIG. 4, FIGS. 11-16 depict cross-sectional views of several possible drug reservoir lumens having different shapes and wall thicknesses. Each housing (110, 120, 130, 140, 150, 160) in FIGS. 11-16 includes a retention frame lumen (113, 123, 133, 143, 153, 163) that is aligned perpendicular to the drug reservoir lumens (111, 121, 131, 141, 151, 161). In other embodiments not shown, the retention frame lumen is aligned parallel to the drug reservoir lumen. The drug reservoir lumens (111, 121, 131, 141, 151, 161) in the housings (110, 120, 130, 140, 150, 160) may have two defined openings—i.e., two opposed openings—as shown in FIGS. 11-13, or one defined opening—i.e., a single opening—as shown in FIGS. 14-16.

In some embodiments, the walls that define the drug reservoir lumens may have varying thickness. Housings with walls of different thicknesses may improve the housing's flexibility, compressibility, or both. Different wall thicknesses also may aid in securing a solid drug unit in the drug reservoir lumens. Examples of drug reservoir lumens with varying walls thicknesses are shown in cross-section in FIGS. 11 and 14. One wall of the drug reservoir lumen (111, 141) is thicker than the other in these embodiments. Although these embodiments depict the thinner wall adjacent to the retention frame lumen (113, 143), other embodiments of the housing may be configured so the thinner wall is on the side that is opposite the retention frame lumen (113, 143).

In some embodiments, the drug reservoir lumens in the devices described herein may have a convex wall. The convex walls may aid in securing a solid drug unit, including a cylindrical solid drug unit, after it is inserted into the drug reservoir lumen. Examples of drug reservoir lumens with convex walls are shown in FIGS. 12 and 15. The convex walls (124, 154) may be made of an elastomer. Convex wall shapes may be produced when a low durometer elastomer sheet is mechanically punched. As used herein, the term "low durometer" refers to a Shore hardness less than 60 A.

In some embodiments, the drug reservoir lumens in the devices described herein may have a concave wall. The concave walls may aid in securing a solid drug unit, including a spherical or ellipsoidal solid drug unit, in a drug reservoir lumen after it is inserted into the drug reservoir lumen. FIGS. 13 and 16 are cross-sectional views of possible drug reservoir lumens (131, 161) with concave walls (134, 164).

Figure 17:
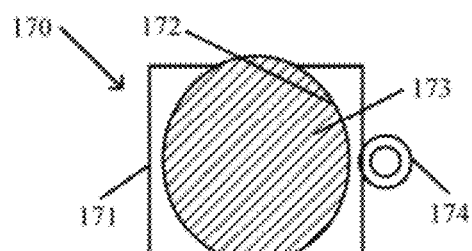
FIG. 17 is a cross-sectional view of one embodiment of a drug reservoir lumen having concave walls and housing a solid drug unit with a diameter larger than the width of the housing.

FIG. 17 is cross-sectional view of another housing 170 with a drug reservoir lumen 171 having concave walls. FIG. 17 shows that a drug reservoir lumen 171 having concave walls 172 may be used to hold a spherical drug tablet 173 having a diameter slightly larger than the height of the housing 170.

Figure 18:
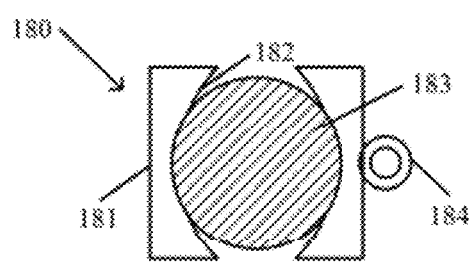
FIG. 18 is a cross-sectional view of one embodiment of a drug reservoir lumen having concave walls and housing a solid drug unit with a diameter smaller than the width of the housing.

FIG. 18 is a cross-sectional view of another housing 180 with a drug reservoir lumen 181 having concave walls 182. FIG. 18 shows that a drug reservoir lumen 181 having concave walls 182 may be used hold a spherical drug tablet 183 having a diameter slightly smaller than the height of the housing 180. The housings (170, 180) shown in FIGS. 17 and 18 also include a retention frame lumen (174, 184) that is aligned perpendicular to the drug reservoir lumens (171, 181) and parallel to the housings' longitudinal axes. In certain embodiments, an elastomeric wall material enables one to insert into a drug reservoir lumen a spherical or ellipsoidal drug unit that has a diameter larger than that of the drug reservoir lumen's opening. The drug reservoir lumen having a concave wall further facilitates retention of such a drug unit.

If the diameter of a solid drug unit is slightly larger than that of a drug reservoir lumen and the wall defining the drug reservoir lumen is made of a low durometer or low stiffness material, then it is easier, in certain embodiments, to insert the drug unit into the drug reservoir lumen if the lumen has a relatively thicker wall construction. Not wishing to be bound by any particular theory, it is believed that this is because the thicker wall may prevent the wall from being entrained, folded, or collapsed during the process of inserting the solid drug unit into the drug reservoir lumen. If a low durometer silicone is used as the material of construction for the housing and a thicker wall is needed for the drug reservoir lumen, then the silicone with a foam or porous structure can be used, in certain embodiments, to reduce the mass of the device. Even with a drug reservoir lumen having a relatively thick wall, the overall cross-section size should still be dimensioned to fit into the lumen of the catheter, cystoscope, or other deployment instrument. Regardless, the housing may be constructed with walls of any thickness.

Wherever possible, all of the features described herein may be applied to any housing, whether monolithic or modular in structure.

Modular Housings

The modular housings are typically formed from at least two separate housing units, each unit housing at least one solid drug unit. The material from which each housing unit is formed defines at least one drug reservoir lumen capable of housing a solid drug unit. The drug reservoir lumens may have one or more defined openings. For example, the drug reservoir lumen may have two opposed openings which expose correspondingly opposed end surfaces of the at least one solid drug unit housed therein.

In certain embodiments, the at least two separate housing units in the modular housings are connected, directly or indirectly, by a retention frame. In some embodiments, the modular housing units may be placed on the retention frame to form a "bracelet" design. The devices may have one housing unit or a plurality of housing units. The number of housing units may be limited only by the size of the retention frame by which they are connected.

In some embodiments, one or more of the separate housing units includes a retention frame lumen through which a shared retention frame is extended. In certain embodiments, the retention frame lumen and the drug reservoir lumen of each housing unit are arranged parallel to each other. In particular embodiments, the retention frame lumen and the drug reservoir lumen of each housing unit are arranged perpendicular to each other. In further embodiments, the retention frame lumen and the drug reservoir lumen of each housing unit are arranged at an angle other than 0° (parallel) and 90° (perpendicular), such as 5, 10, 30, 45, 60, or 85°. In further embodiments, the devices described herein include two or more housing units with at least two of the following configurations: (1) the retention frame lumen and drug reservoir lumen are arranged substantially parallel to each other, (2) the retention frame lumen and drug reservoir lumen are arranged substantially perpendicular to each other, and (3) the retention frame lumen and drug reservoir lumen are arranged at an angle other than 0° (parallel) and 90° (perpendicular).

Figure 19:
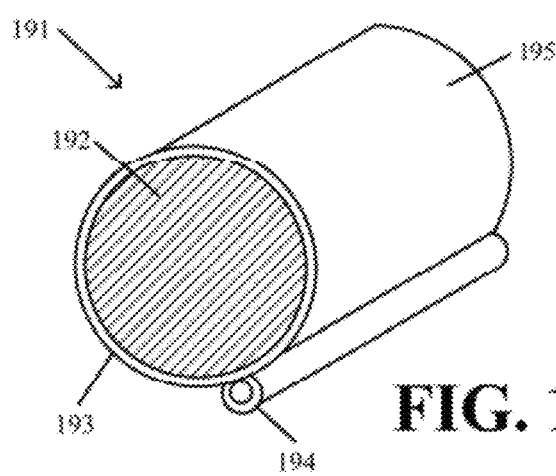
FIG. 19 is a depiction of one embodiment of a modular housing unit having a drug reservoir lumen and a retention frame lumen.

FIG. 19 is a perspective view of one embodiment of a drug housing unit 191, which contains a drug tablet 192. The walls of the drug housing unit define a drug reservoir lumen 193 and a retention frame lumen 194. In this embodiment, the drug reservoir lumen 193 and the retention frame lumen 194 are oriented parallel to one another. The wall of the drug housing unit 195 defining the drug reservoir lumen 193 encases the cylindrical surface of the drug tablet 192. In this embodiment, both ends of the housing unit 191 have a defined opening that exposes opposite surface areas (the ends) of the solid drug tablet 192. In an embodiment not shown, the drug housing unit has only one defined opening.

Generally, the modular housing units described herein can contain one or more solid drug units, such as tablets or capsules. The wall, or casing, material may, but need not, be water permeable or drug permeable. If the wall is impermeable to drug, then the surface area of the drug in contact with urine or other bodily fluids affects drug release rate. Multiple housing units may be connected to a retention frame to form the drug housing, and achieve a selected drug release rate.

Generally, the housing units may be formed integrally, such as via molding or extrusion, although separate construction and assembly of the lumen walls is possible. The wall that defines the retention frame lumen, if present, may extend along the entire length of the wall that defines the drug reservoir lumen, so that the retention frame lumen has the same length as the drug reservoir lumen as shown in FIG. 19, although one wall may be shorter than the other wall in other embodiments. Further, the two walls may be attached along the entire length of the device in the illustrated embodiment, although intermittent attachment can be employed.

Figure 20:
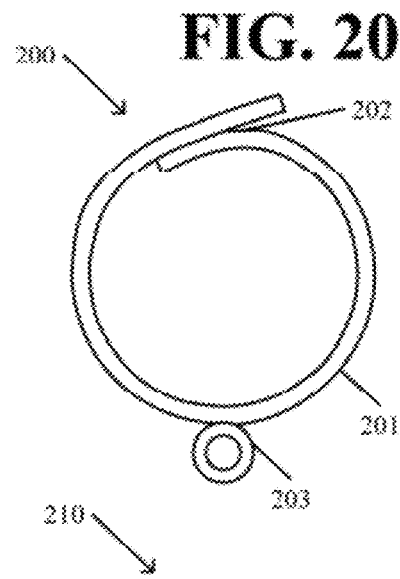
FIG. 20 is a depiction of one embodiment of a modular housing unit that shows the attachment of overlapping portions of the drug reservoir lumen's walls.
Figure 21:
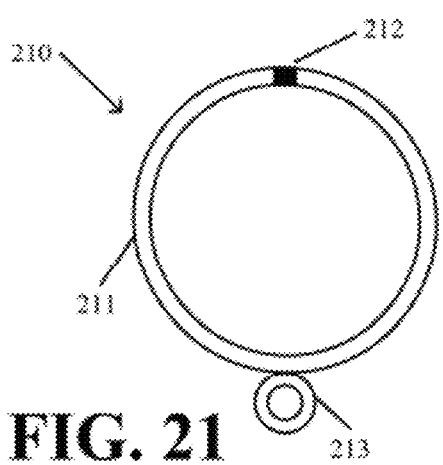
FIG. 21 is a depiction of one embodiment of a modular housing unit that shows the attachment of the ends of the walls that form the drug reservoir lumen.
Figure 22:
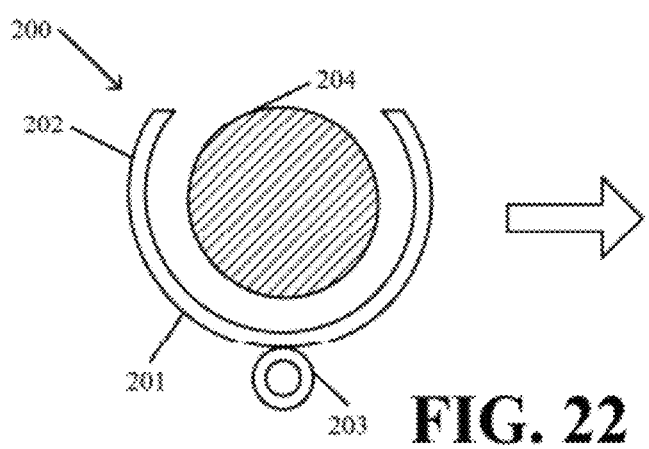
FIG. 22 is a depiction of one method for making a modular housing unit.

FIGS. 20-22 depict how a housing unit (200, 210), such as the one shown FIG. 19, can be formed and loaded with a solid drug unit, in certain embodiments. A drug reservoir lumen (201, 211) can be formed by rolling a flexible film or sheet (e.g., an elastic film or sheet) and sealing the overlapping edges 202 (FIG. 20) or adjacent edges 212 (FIG. 21) together using any method of attachment know in the art, including adhesives or chemical bonding, or interlocking tabs or other mechanical connectors. Silicone adhesive or other medical grade adhesive can be used. FIG. 22 shows that an assembly process for loading a drug tablet 204 into the drug reservoir lumen 201 of the housing unit 200 of FIG. 20. In FIG. 20, the drug reservoir lumen 201 is formed by affixing one side of the film or sheet to the overlapping portion 202 of the other. Each housing unit shown in FIGS. 20-22 includes a retention frame lumen (203, 213) that is aligned parallel to the drug reservoir lumens (201, 211). In other embodiments, the housing units may be aligned perpendicular to the drug reservoir lumens.

Figure 23:
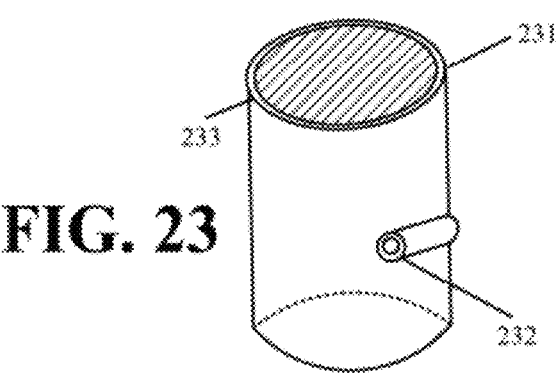
FIG. 23 is a depiction of a modular housing unit having two defined openings and a retention frame lumen.

FIG. 23 is a perspective view of another embodiment of a housing unit that can be used in the modular housings described herein. The housing unit 230 of FIG. 23 contains a drug tablet 233. In this embodiment, the drug reservoir lumen 231 and the retention frame lumen 232 are oriented perpendicular to one another. In this embodiment, both ends of the drug reservoir lumen have a defined opening that exposes a surface area of the drug tablet 233. In another embodiment not shown, the drug reservoir lumen has only one defined opening. In the embodiment shown, the defined openings of the drug reservoir lumen 231 will be substantially perpendicular to the longitudinal axis of the device.

Figure 24:
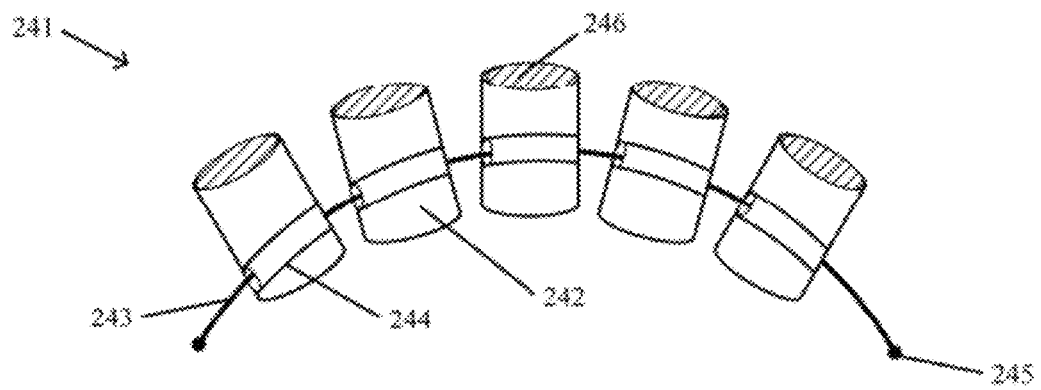
FIG. 24 is a depiction of one embodiment of a device having modular housing units connected by a retention frame.

FIG. 24 shows a particular embodiment of the device 241 in which several of the housing units 242 shown in FIG. 23 are connected together by a retention frame 243 extending through the retention frame lumens 244 of the housing units, which encase a solid drug unit 246. The retention frame 243 includes a circular cap 245 to improve tolerability of the device. In the embodiment shown, the housing units are immovably attached to the retention frame. In another embodiment not shown, the housing units are allowed to slide and/or rotate about the retention frame.

Generally, the retention frame of the modular housings may include an enlarged portion at its ends to prevent the end of the retention frame from passing through the retention frame lumen of at least the terminal housing units. Typically, the enlarged portion should have a size that exceeds the smallest diameter of the retention frame lumen of at least the terminal housing units. The retention frame itself may be shaped to form the enlarged portion, or a capping material can be placed on the end of the retention frame. Alternatively or additionally, the end portions of the retention frame preferably are rounded and/or capped with soft material to facilitate patient tolerability of the inserted device.

In some embodiments, the retention frame does not include an enlarged portion at its ends to prevent the end of the retention frame from passing through the retention frame lumen of at least the terminal housing units. The enlarged portion is not needed in certain embodiments, because the housing units may be immovably attached to the retention frame, such as with friction or an adhesive. As used herein, "immovably attached" means that the housing units are affixed so that they cannot (1) rotate about the retention frame, (2) slide along the longitudinal axis of the retention frame, or (3) rotate about and slide along the retention frame.

The housing units may be oriented with reference to the retention frame such that, when in the retention shape, the housing lies within the perimeter of the retention frame, beyond the perimeter of the retention frame, or a combination thereof.

Figure 25:
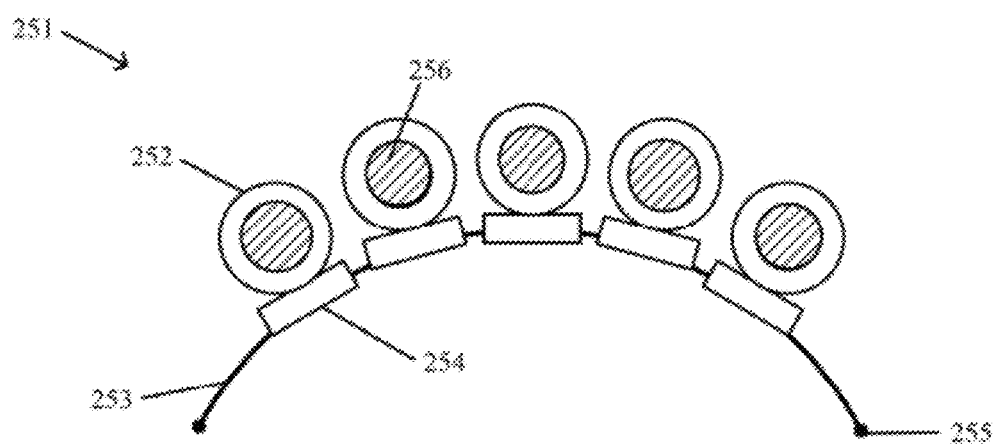
FIG. 25 is a depiction of one embodiment of a device having modular housing units connected by a retention frame.

In FIG. 25, an embodiment of the device 251 is shown in which the retention frame 253 does not include enlarged portions at its ends because the housing units 252, which encase a solid drug unit 256, are immovably attached to the retention frame 253. The retention frame 253 includes end caps 255 to improve the device's tolerability. Unlike the embodiment shown in FIG. 24, each housing unit in the embodiment shown in FIG. 25 is positioned outside the arc of the retention frame 253. Alternatively, in an embodiment that is not shown, each housing unit in FIG. 25 may be rotated 180 degrees about the retention frame and positioned inside of the arc of the retention frame.

In some embodiments, the modular housing units may be uniformly oriented at any degree about the retention frame. In other embodiments, one or more modular housing units may be oriented at different degrees about the retention frame.

Figure 26:
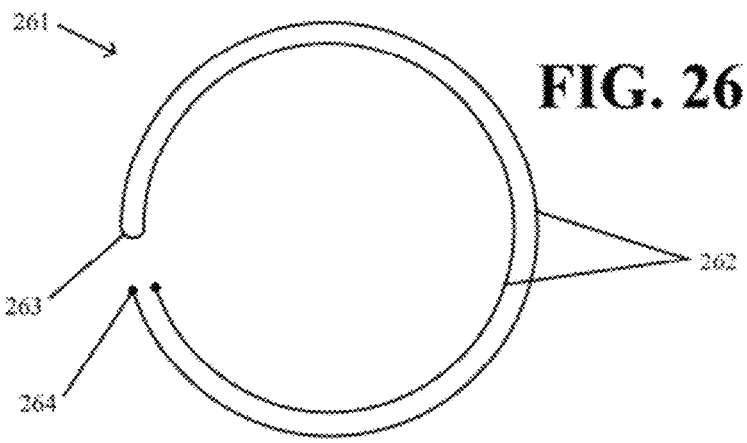
FIG. 26 is a depiction of one embodiment of a retention frame.

Generally, the retention frame may be of any shape that is capable of forming the retention shape, thereby retaining the device in the lumen or body cavity into which it is deployed. FIG. 26 is a perspective view of one embodiment of a retention frame 261, which has two parallel, circular parts 262 formed of a single wire element, the circular parts being connected by a sharp bend 263 and having two end caps 264. This figure shows the retention frame in its retention shape suited to retain the device within the body cavity. The retention frame 261 may be formed of a superelastic alloy wire or strip, such as nitinol.

Figure 27:
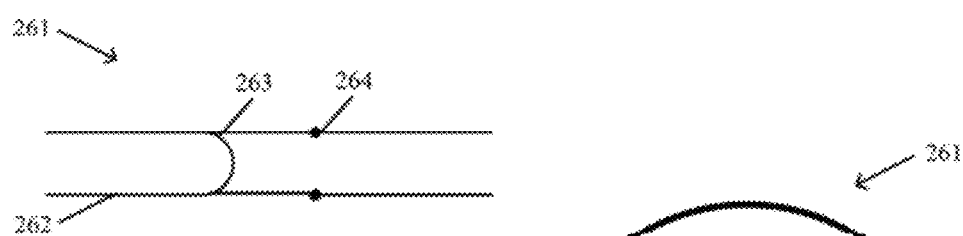
FIG. 27 is a depiction of a side view of an embodiment of the retention frame shown in FIG. 26.
Figure 28:
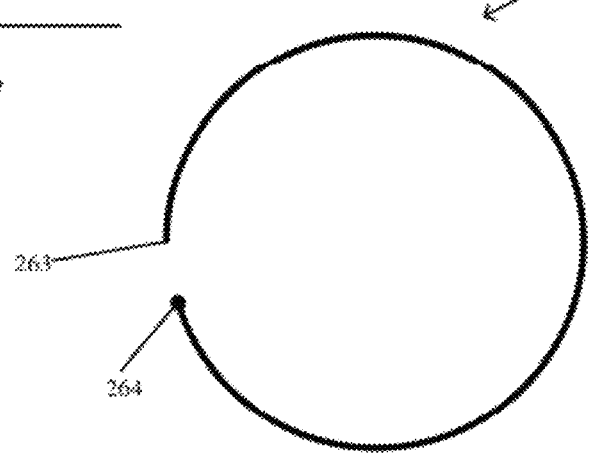
FIG. 28 is a depiction of a top view of an embodiment of the retention frame shown in FIG. 26.
Figure 29:
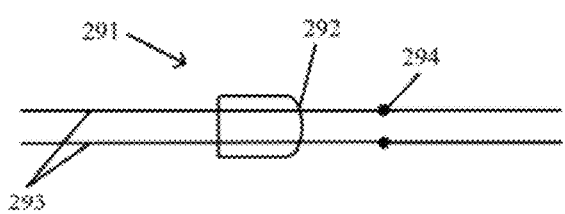
FIG. 29 is a depiction of a side view of an embodiment of a retention frame.
Figure 30:
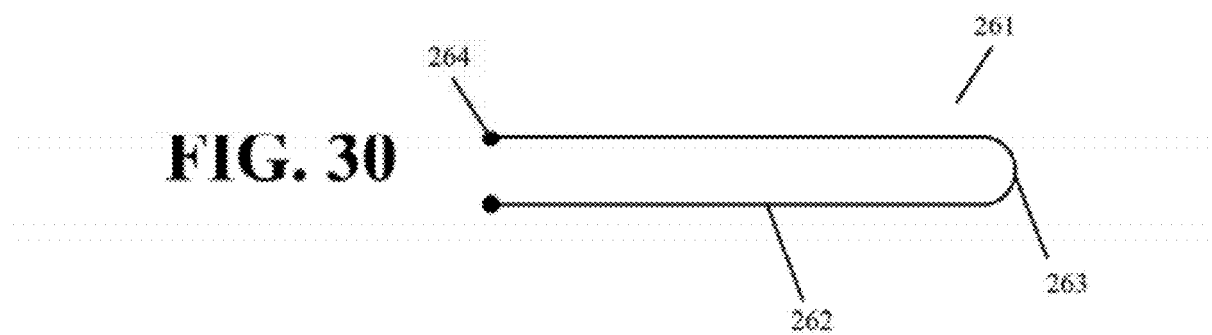
FIG. 30 is a depiction of the retention frame of FIG. 26 in a relatively straightened shape.

FIG. 27 and FIG. 28 provide a side view and a top view, respectively, of the device shown in FIG. 26. FIG. 29 is a side view of an alternative embodiment of a retention frame 291 in which the sharp bend of FIGS. 26-28 is replaced with a turn 292, which connects the two circular parts 293, which terminate with end caps 294. FIG. 30 depicts the retention frame 261 of FIG. 26, but in a relatively straightened shape suited for insertion through a lumen into a body cavity of a patient, for example through the patient's urethra into the bladder.

Generally, the housing units of the modular housings described herein may have one or more retention frame lumens for housing the various retention frame designs. For example, as shown in the perspective view of FIG. 31, a modular housing unit 311 may have two retention frame lumens 312a, 312b. In this particular embodiment, the two retention frame lumens 312a, 312b are parallel to one another and to the drug reservoir lumen 313, which houses a solid drug unit 314. In the embodiment shown, the drug reservoir lumen 313 has two defined openings. In an embodiment not shown, the drug reservoir lumen has one defined opening.

Figure 32:
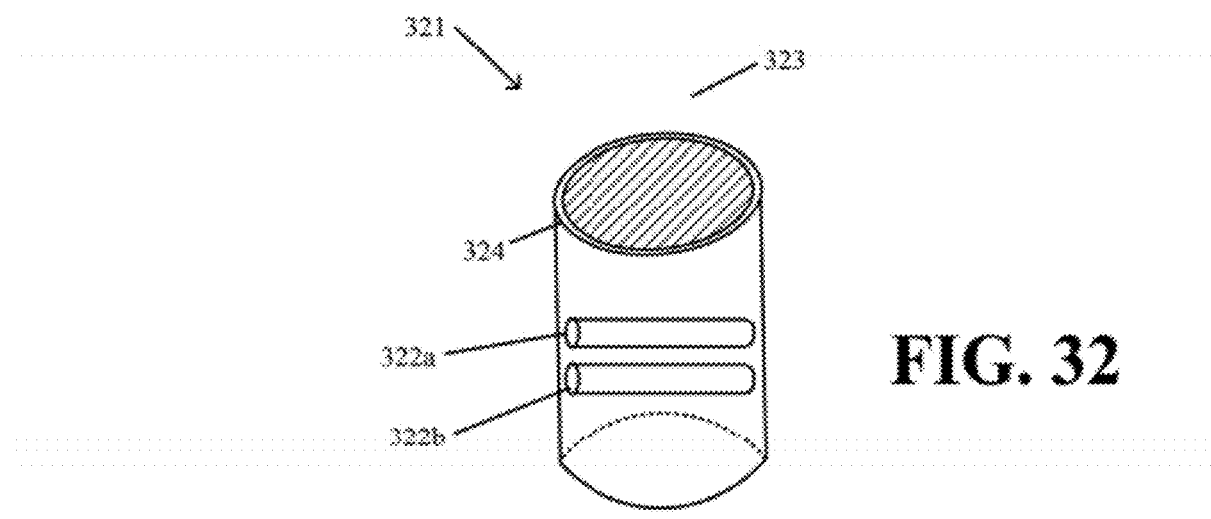
FIG. 32 is a depiction of one embodiment of a modular housing unit having two retention frame lumens.

Another embodiment of a modular housing unit is shown in FIG. 32, which is a perspective view of a modular housing unit 321 that has two retention frame lumens 322a, 322b. In this embodiment, the two retention frame lumens 322a, 322b are parallel to one another and perpendicular to the drug reservoir lumen 323, which houses a solid drug unit 324. In the embodiment shown, the modular housing unit has two defined openings. In an embodiment not shown, the modular housing unit has one defined opening.

Figure 31:
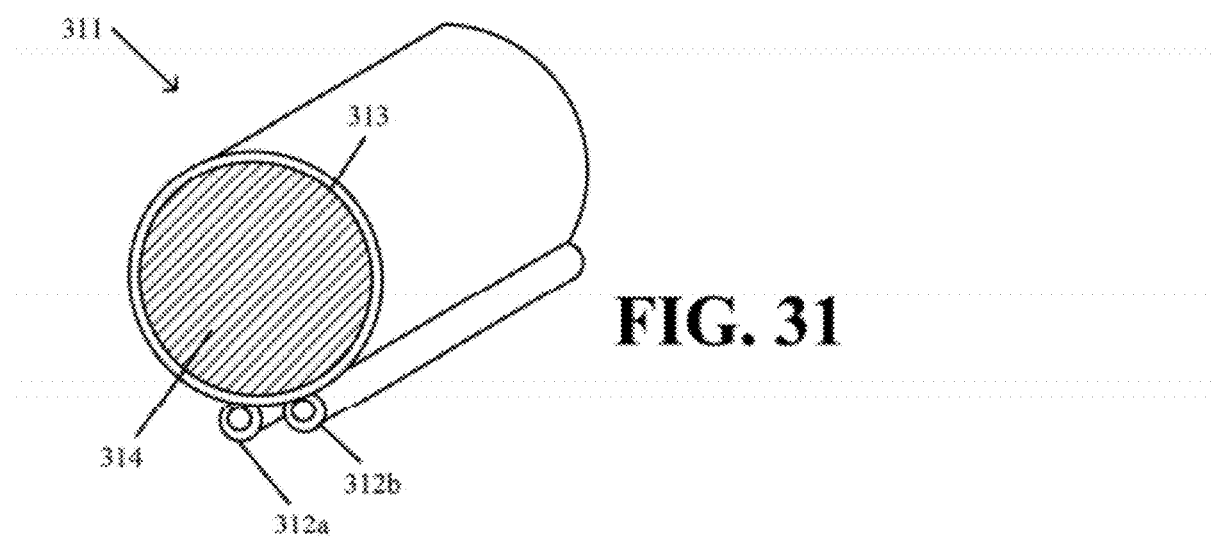
FIG. 31 is a depiction of one embodiment of a modular housing unit having two retention frame lumens.
Figure 33:
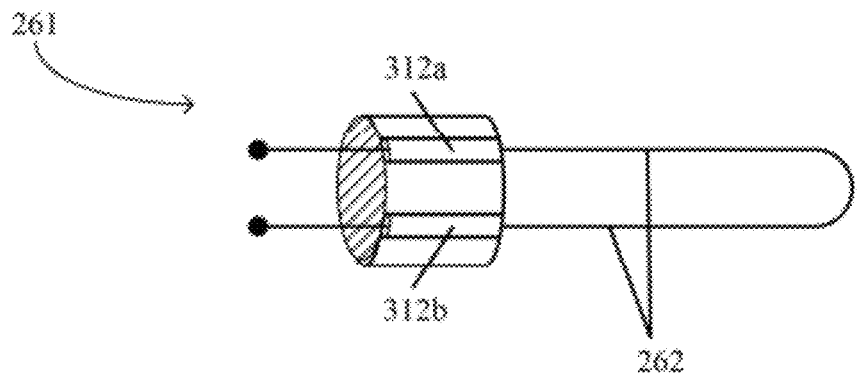
FIG. 33 is a depiction of one embodiment of a retention frame in a relatively straightened shape onto which a modular housing unit has been arranged.
Figure 34:
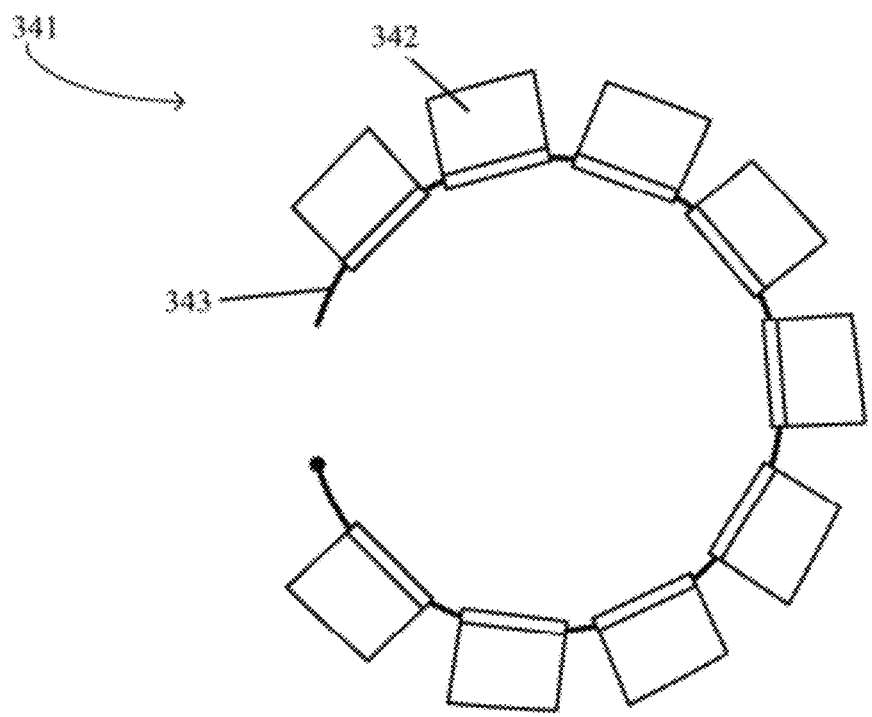
FIG. 34 is a depiction of one embodiment of a device having modular housing units connected by a retention frame.

The embodiments of the housing units shown in FIGS. 31 and 32 may be used with the retention frame embodiments shown in FIGS. 26-29. For example, FIG. 33 shows a single housing unit of the embodiment shown in FIG. 31, wherein each of the retention frame lumens (312a, 312b) is threaded by one of the long segments 262 of the retention frame 261 of FIG. 30, which is in the relatively straightened shape suited for insertion through a lumen into a body cavity of a patient. In this embodiment, the retention frame is elastic and will return to the retention shape suited to retain the device within the body cavity as shown in FIG. 34, which depicts an assembled device 341, wherein nine housing units 342 are threaded onto the retention frame 343, and the device is in its retention shape.

Figure 35:
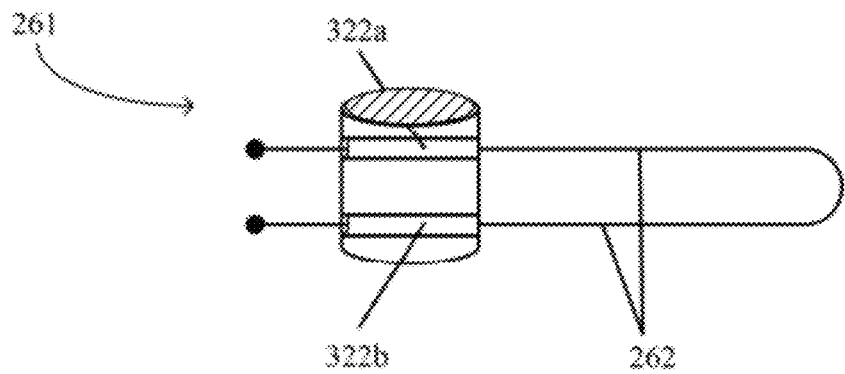
FIG. 35 is a depiction of one embodiment of a retention frame in a relatively straightened shape onto which a modular housing unit has been arranged.
Figure 36:
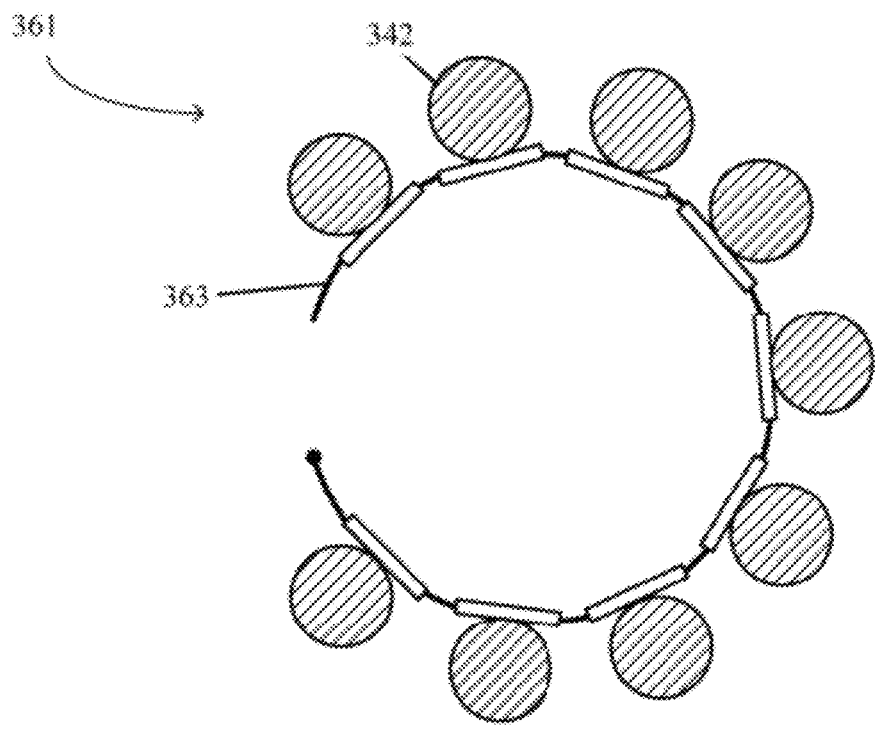
FIG. 36 is a depiction of a one embodiment of a device having modular housing units connected by a retention frame.

Similarly, FIG. 35 shows a single housing unit of the embodiment shown in FIG. 32, wherein each of the retention frame lumens (322a, 322b) is threaded by one of the long segments 262 of the retention frame of FIG. 30, which is in the relatively straightened shape suited for insertion through a lumen into a body cavity of a patient. In one embodiment, the retention frame is elastic and will return to the retention shape suited to retain the device within the body cavity as shown in FIG. 36, which depicts an assembled device 361, wherein nine housing units 362 are threaded onto the retention frame 363, and the device is in its retention shape. Although these embodiments include nine housing units, the devices herein may include one housing unit or the largest number of housing units that will fit on a particular retention frame.

In certain embodiments, it may be desirable to maintain a selected space between adjacent housing units. In some embodiments, for example, spacers may be used to ensure that the housing units' defined openings are not partially or completely interrupted by the adjacent housing units. Generally, the spacers can have one or more lumens that accommodate the passage of a retention frame through the spacer. Like the housing units, the spacers may or may not be immovably fixed to the retention frame. The spacers generally may be made from silicone or another biocompatible material.

FIG. 37 shows one embodiment of the drug delivery device 371 in which spacer elements 374 (i.e., spacers) are provided between the housing units 372 that are connected via the retention frame 373. The spacer may be useful when, in certain embodiments, the curvature of the retention frame is small. FIGS. 38 and 39 are perspective views of two possible designs for spacers, such as those shown in FIG. 37. In FIG. 38, the spacer 381 has two separate, parallel lumens 38, through each of which one of the retention frame segments may be disposed. In FIG. 39, the spacer 391 has a single, relatively larger and oval lumen 392, through which both segments of the retention frame may be disposed. The spacers may be placed between alternate modular housing units or at any other interval.

Although the monolithic housings and modular housings have been explained separately in this disclosure, the features described herein, where possible, can be applied to both types of devices. Moreover, hybrid devices that include housings that are part monolithic and part modular also are envisioned.

Any of the defined openings or ends of the housings, including the monolithic housing and modular housing units, may be sealed, if desired to close off an opening. This sealing may be accomplished with a sealing substance or structure. The sealing structure may be formed of biocompatible material, including a metal such as stainless steel, a polymer such as silicone, a ceramic, or sapphire, or adhesive, among others or combinations thereof. The sealing substance or structure may be biodegradable or bioerodible. In one embodiment, a medical grade silicone adhesive or other adhesive is loaded into the opening in a fluid or workable form and then cure within the housing opening to seal it.

Whether a particular device has a monolithic or modular housing, the devices described herein can have any size that permits insertion into a lumen and body cavity, such as the urethra and bladder, respectively.

The devices may be inserted into a patient using a cystoscope or catheter. Typically, a cystoscope for an adult human has an outer diameter of about 5 mm and a working channel having an inner diameter of about 2.4 mm to about 2.6 mm. In embodiments, a cystoscope may have a working channel with a larger inner diameter, such as an inner diameter of 4 mm or more. Thus, the device may be relatively small in size. For example, when the device is elastically deformed to the relatively straightened shape, the device for an adult patient may have a total outer diameter that is less than about 2.6 mm, such as between about 2.0 mm and about 2.4 mm. For pediatric patients, the dimensions of the device are anticipated to be smaller, e.g., proportional for example based on the anatomical size differences and/or on the drug dosage differences between the adult and pediatric patients. In addition to permitting insertion, the relatively small size of the device may also reduce patient discomfort and trauma to the bladder.

In one embodiment, the overall configuration of the device promotes in vivo tolerability for most patients. In a particular embodiment, the device is configured for tolerability based on bladder characteristics and design considerations described in U.S. Application Publication No. 2011/0152839 (TB 112), which is incorporated herein by reference.

Within the three-dimensional space occupied by the device in the retention shape, the maximum dimension of the device in any direction preferably is less than 10 cm, the approximate diameter of the bladder when filled. In some embodiments, the maximum dimension of the device in any direction may be less than about 9 cm, such as about 8 cm, 7 cm, 6 cm; 5 cm, 4.5 cm, 4 cm, 3.5 cm, 3 cm, 2.5 or smaller. In particular embodiments, the maximum dimension of the device in any direction is less than about 7 cm, such as about 6 cm, 5 cm, 4.5 cm, 4 cm, 3.5 cm, 3 cm, 2.5 cm or smaller. In preferred embodiments, the maximum dimension of the device in any direction is less than about 6 cm, such as about 5 cm, 4.5 cm, 4 cm, 3.5 cm, 3 cm, 2.5 cm or smaller. More particularly, the three-dimension space occupied by the device is defined by three perpendicular directions. Along one of these directions the device has its maximum dimension, and along the two other directions the device may have smaller dimensions. For example, the smaller dimensions in the two other directions may be less than about 4 cm, such as about 3.5 cm, 3 cm, 2.5 cm or less. In a preferred embodiment, the device has a dimension in at least one of these directions that is less than 3 cm.

In some embodiments, the device may have a different dimension in at least two of the three directions, and in some cases in each of the three directions, so that the device is non-uniform in shape. Due to the non-uniform shape, the device may be able to achieve an orientation of reduced compression in the empty bladder, which also is non-uniform in shape. In other words, a particular orientation of the device in the empty bladder may allow the device to exert less contact pressure against the bladder wall, making the device more tolerable for the patient.

The overall shape of the device may enable the device to reorient itself within the bladder to reduce its engagement or contact with the bladder wall. For example, the overall exterior shape of the device may be curved, and all or a majority of the exterior or exposed surfaces of the device may be substantially rounded. The device also may be substantially devoid of sharp edges, and is exterior surfaces may be formed from a material that experiences reduced frictional engagement with the bladder wall. Such a configuration may enable the device to reposition itself within the empty bladder so that the device applies lower contact pressures to the bladder wall. In other words, the device may slip or roll against the bladder wall into a lower energy position, meaning a position in which the device experiences less compression.

An example of a device that generally satisfies these characteristics is shown in FIG. 1. In particular, the illustrated device is generally planar in shape even though the device occupies three-dimensional space. Such a device may define a minor axis, about which the device is substantially symmetrical, and a major axis that is substantially perpendicular to the minor axis. The device may have a maximum dimension in the direction of the major axis that does not exceed about 6 cm, and in particular embodiments is less than 5 cm, such as about 4.5 cm, about 4 cm, about 3.5 cm, about 3 cm, or smaller. The device may have a maximum dimension in the direction of the minor axis that does not exceed about 4.5 cm, and in particular embodiments is less than 4 cm, such as about 3.5 cm, about 3 cm, or smaller. The device is curved about substantially its entire exterior perimeter in both a major cross-sectional plane and a minor cross-sectional plane. In other words, the overall exterior shape of the device is curved and the cross-sectional shape of the device is rounded. Thus, the device is substantially devoid of edges, except for edges on the two flat ends, which are completely protected within the interior of the device when the device lies in a plane. These characteristics enable the device to reorient itself into a position of reduced compression when in the empty bladder.

The device also may be small enough in the retention shape to permit intravesical mobility. In particular, the device when deployed may be small enough to move within the bladder, such as to move freely or unimpeded throughout the entire bladder under most conditions of bladder fullness, facilitating patient tolerance of the device. Free movement of the device also facilitates uniform drug delivery throughout the entire bladder.

The device also may be configured to facilitate buoyancy, such as with the use of low density materials of construction for the housing components and/or by incorporating gas or gas generating materials into the housing, as described for example in U.S. Application No. 13/267,560, filed Oct. 6, 2011 (TB 116), which is incorporated herein by reference. In general, the device in the dry and drug-loaded state may have a density in the range of about 0.5 g/mL to about 1.5 g/mL, such as between about 0.7 g/mL to about 1.3 g/mL. In some embodiments, the device in the dry and drug-loaded state has a density that is less than 1 g/mL.

The implantable drug delivery device can be made to be completely or partially bioerodible so that no explantation, or retrieval, of the device is required following release of the drug formulation. In some embodiments, the device is partially bioerodible so that the device, upon partial erosion, breaks into non-erodible pieces small enough to be excreted from the bladder. As used herein, the term "bioerodible" means that the device, or part thereof, degrades in vivo by dissolution, enzymatic hydrolysis, erosion, resorption, or combinations thereof. In one embodiment, this degradation occurs at a time that does not interfere with the intended kinetics of release of the drug from the device. For example, substantial erosion of the device may not occur until after the drug formulation is substantially or completely released. In another embodiment, the device is erodible and the release of the drug formulation is controlled at least in part by the degradation or erosion characteristics of the erodible device body. The devices described herein may be designed to conform with the characteristics of those described in U.S. Application No. 13/267,469, filed Oct. 6, 2011 (TB 117), which is incorporated herein by reference.

Useful biocompatible erodible materials of construction are known in the art. Examples of suitable such materials include synthetic polymers selected from poly(amides), poly (esters), poly(ester amides), poly(anhydrides), poly(orthoesters), polyphosphazenes, pseudo poly(amino acids), poly (glycerol-sebacate)(PGS), copolymers thereof, and mixtures thereof. In a preferred embodiment, the resorbable synthetic polymers are selected from poly(lactic acids), poly(glycolic acids), poly(lactic-co-glycolic acids), poly(caprolactones), and mixtures thereof. Other curable bioresorbable elastomers include poly(caprolactone) (PC) derivatives, amino alcohol-based poly(ester amides) (PEA) and poly (octane-diol citrate) (POC). PC-based polymers may require additional cross-linking agents such as lysine diisocyanate or 2,2-bis($\epsilon$-caprolacton-4-yl)propane to obtain elastomeric properties.

Alternatively, the implantable drug delivery device may be at least partially non-bioerodible. It may be formed of medical grade silicone tubing, as known in the art. Other examples of suitable non-resorbable materials include synthetic polymers selected from poly(ethers), poly(acrylates), poly(methacrylates), poly(vinyl pyrolidones), poly(vinyl acetates), poly(urethanes), celluloses, cellulose acetates, poly(siloxanes), poly(ethylene), poly(tetrafluoroethylene) and other fluorinated polymers, poly(siloxanes), copolymers thereof, and combinations thereof. Following release of the drug formulation, the device and/or the retention frame may be removed substantially intact or in multiple pieces.

The drug delivery device may be sterilized before being inserted into a patient. In one embodiment, the device is sterilized using a suitable process such as gamma irradiation or ethylene oxide sterilization, although other sterilization processes may be used.

Retention of the Device in a Body Cavity

The devices described herein are elastically deformable between a relatively straightened shape suited for insertion through a lumen into a body cavity of a patient and a retention shape suited to retain the device within the body cavity. In certain embodiments, the drug delivery device may naturally assume the retention shape and may be deformed, either manually or with the aid of an external apparatus, into the relatively straightened shape for insertion into the body. Once deployed the device may spontaneously or naturally return to the initial, retention shape for retention in the body:

For example, the device shown in FIG. 1, is depicted in a retention shape suited to retain the device within a body cavity. In contrast, the portion of the device shown in FIG. 2 is in a relatively straightened shape suited for insertion through a lumen into a body cavity of a patient. Following deployment into the body, the device may assume the retention shape to retain the drug delivery device in the body cavity or lumen.

For the purposes of this disclosure, the term "retention shape" generally denotes any shape suited for retaining the device in the intended implantation location, including, but not limited to, the pretzel shape shown in FIG. 1, which is suited for retaining the device in the bladder. Similarly, the term "relatively straightened shape" generally denotes any shape suited for deploying the drug delivery device into the body, including, but not limited to, the linear or elongated shape shown in FIG. 2, which is suited for deploying the device through the working channel of catheter, cystoscope, or other deployment instrument positioned in a lumen of the body, such as the urethra.

In some embodiments, the drug delivery devices do not need a retention frame to be elastically deformable between a relatively straightened shape and a retention shape. In these embodiments, the material from which the housing is formed makes the device capable of being elastically deformed between the two shapes.

In other embodiments, the drug delivery devices include a retention frame that is associated with the housing. The properties of the retention frame cause the device to function as a spring, deforming in response to a compressive load but spontaneously returning to its initial shape once the load is removed.

The housing may include one or more retention frame lumens through which portions of a retention frame are threaded. In some embodiments, the housing does not include a retention frame lumen, and the retention frame is affixed to the housing any other means, such as an adhesive.

In certain embodiments, the retention frame, like the devices themselves, may naturally assume the retention shape, may be deformed into the relatively straightened shape, and may spontaneously return to the retention shape upon insertion into the body. The retention frame in the retention shape may be shaped for retention in a body cavity, and the retention frame in the relatively straightened shape may be shaped for insertion into the body through the working channel of a deployment instrument such as a catheter or cystoscope. To achieve such a result, the retention frame may have an elastic limit, modulus, and/or spring constant selected to impede the device from assuming the relatively lower-profile shape once implanted. Such a configuration may limit or prevent accidental expulsion of the device from the body under expected forces. For example, the device may be retained in the bladder during urination or contraction of the detrusor muscle.

In a preferred embodiment, the device is elastically deformable between a relatively straightened shape suited for insertion through a catheter or cystoscope extending through a patient's urethra of a patient and a curved or coiled shape suited to retain the device within the bladder (i.e., to prevent its expulsion from the bladder during urination) following release of the device from the end of the catheter or cystoscope. In a particular configuration of this embodiment, the device has an elastic wire or strip serving as the retention frame, and the elastic wire or strip acts as a spring to maintain the device in the curved or coiled shape in the absence of a compressive load on the device and when the device is under compression from the bladder walls during urination or other contraction of the patient's detrusor muscle.

In certain embodiments, the retention frame includes or consists of an elastic wire or an elastic strip. In one embodiment, the elastic wire may comprise a biocompatible shape-memory material or a biodegradable shape memory polymer as known in the art. The elastic wire also may include a relatively low modulus elastomer, which may be relatively less likely to irritate or cause ulcer within the bladder or other implantation site and may be biodegradable so that the device need not be removed. Examples of low modulus elastomers include polyurethane, silicone, styrenic thermoplastic elastomer, and poly(glycerol-sebacate) (PGS). The elastic wire may be coated with a biocompatible polymer, such as a coating formed from one or more of silicone, polyurethane, styrenic thermoplastic elastomer, Silitek, Tecoflex, C-flex, and Percuflex.

For example, in the embodiment shown in FIGS. 1-3, the retention frame is an elastic wire formed from a superelastic alloy, such as nitinol, and surrounded by the wall of the retention frame lumen 14, which forms a protective sheath about the retention frame in this embodiment. The wall may be formed from a polymer material, such as silicone. In other embodiments, the retention frame may be an elastic wire formed from a superelastic alloy, such as nitinol, that is covered in a polymer coating, such as a silicone sheath, and is attached to the housing. In some embodiments, the retention frame may be an elastic strip, such as an elastic strip formed from a superelastic alloy.

In some embodiments, the retention frame lumen may include the retention frame and a filling material, such as a silicone adhesive, such as MED3-4213 by Nusil Technology LLC, although other filling materials may be used. The filling material is optional and may be omitted; however, its inclusion may fill the void in the retention frame lumen about the retention frame and may reduce the tendency of the drug reservoir lumen to stretch along, or twist or rotate about, the retention frame, while maintaining the drug reservoir lumen in a selected orientation with reference to the retention frame.

A retention frame that assumes a pretzel shape, such as in FIG. 1, may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

In embodiments in which the retention frame (or the housing itself in embodiments without a retention frame) comprises a shape-memory material, the material used to form the frame may "memorize" and spontaneously assume the retention shape upon the application of heat to the device, such as when exposed to body temperatures upon entering the bladder.

A high modulus material may be used for the retention frame in some embodiments, or, in other embodiments, a low modulus material. When a low-modulus material is used, the retention frame may have a diameter and/or shape that provides a spring constant without which the frame would significantly deform under the forces of urination. For example, the retention frame may include one or more windings, coils, spirals, or combinations thereof, specifically designed to achieve a desirable spring constant, such as a spring constant in the range of about 3 N/m to about 60 N/m, or more particularly, in the range of about 3.6 N/m to about 3.8 N/m. Such a spring constant may be achieved by one or more of the following techniques: increasing the diameter of the elastic wire used to form the frame, increasing the curvature of one or more windings of the elastic wire, and adding additional windings to the elastic wire. The windings, coils, or spirals of the frame may have a number of configurations. For example, the frame may be in a curl configuration comprising one or more loops, curls or sub-circles. The ends of the elastic wire may be adapted to avoid tissue irritation and scarring, such as by being soft, blunt, inwardly directed, joined together, or a combination thereof.

The retention frame may have a two-dimensional structure that is confined to a plane, a three-dimensional structure, such as a structure that occupies the interior of a spheroid, or some combination thereof. The frames may comprise one or more loops, curls, or sub-circles, connected either linearly or radially, turning in the same or in alternating directions, and overlapping or not overlapping. The frames may comprise one or more circles or ovals arranged in a two-dimensional or a three-dimensional configuration, the circles or ovals either closed or opened, having the same or different sizes, overlapping or not overlapping, and joined together at one or more connecting points. The retention frame portion also may be a three-dimensional structure that is shaped to occupy or wind about a spheroid-shaped space, such as a spherical space, a space having a prorate spheroid shape, or a space having an oblate spheroid shape. Retention frame portions may be shaped to occupy or wind about a spherical space. The retention frame portion may generally take the shape of two intersecting circles lying in different planes, two intersecting circles lying in different planes with inwardly curled ends, three intersecting circles lying in different planes, or a spherical spiral. In each of these examples, the retention frame portion can be stretched to the linear shape for deployment through a deployment instrument. The retention frame portion may wind about or through the spherical space, or other spheroid-shaped space, in a variety of other manners. One or both of the retention frame and retention frame lumen may be omitted, in which case the housing itself may assume or may be deformed into any retention shape described herein. Examples of alternative configurations are described in the U.S. patent applications incorporated by reference herein.

II. Drug Release

The drug from the solid drug units in the devices described herein can be released over an extended period. The release rate of the drug from the drug reservoir portion generally is controlled by the design of the combination of the device components, including but not limited to the materials, dimensions, exposed surface area of the solid drug units, and defined openings of the housing, as well as the particular drug formulation and total mass of drug load, among others. In some embodiments, release of drug is controlled by dissolution, diffusion, or a combination thereof.

In certain embodiments, the housings are configured to expose a constant surface area of the solid units at the defined opening as the solid drug units are dissolved at the exposed surface area. The use of the term "housing" throughout the specification encompasses both monolithic and modular housings, unless otherwise noted. By increasing or decreasing the size of the defined openings in the housings, the rate of drug release can be controlled in these embodiments. In an embodiment of the device designs described herein, erosion of the drug tablets at the one or more exposed surfaces governs the rate of drug release.

In some embodiments, the housings can be configured to permit segregating two or more different drugs, or two or more different formulations of the same drug, in different reservoirs. These embodiments can be combined and varied to achieve a desired release profile and/or combination therapy.

In some embodiments, the onset of release of two doses in different reservoirs can be staged by configuring the device accordingly. The device may release some drug relatively quickly after implantation while other drug may experience an induction time before beginning release.

An example of a drug delivery device is shown in FIG. 1. As shown, the device 10 includes a number of solid drug units 12 that are housed in separate tube portions 13 separated by gaps. The ends of the tube segments have defined openings (6a, 6b), which expose surface areas of the solid drug units. In one embodiment, when the device is deployed in the bladder, water or urine contacts the drug units at the surface areas. Optionally, the device may be configured such that water or urine also permeates through the wall of the tube segments, through one or more apertures in the sidewall of the tube segments, or through passing pores formed through a porous tube segment. The material from which the tube is made also may be drug permeable. The water or urine in contact with the solid drug unit causes the drug to be solubilized. The solubilized drug is diffused, in this embodiment, from the device at a controlled rate. The rate of dissolution of the drug may limit or control the rate at which the drug is dispensed from the device. The rate of dissolution, and therefore diffusion, may be adjusted by increasing or decreasing the size of the defined openings, using a porous material to form the housing, using a water permeable material to form the housing, using a drug permeable material to form the housing, or a combination thereof.

In addition to adjusting the sizes of the defined openings, the defined openings of the housings, in some embodiments, may be positioned to facilitate drug release in a particular portion of a body cavity, such as the bladder. For example, the defined openings of the housings may be positioned inside the perimeter of the device, outside of the perimeter of the device, or on an upper or lower plane of the device. An opening positioned on the inside perimeter or on the upper or lower plane of the device may be less likely to become positioned directly adjacent to a portion of the implantation site, such as the bladder wall, delivering a relatively larger quantity of drug to one particular area of the urothelium. Accordingly, such inside perimeter positioning of openings may be advantageous when uniform administration to all of the urothelium is desired.

The drug release rate also may be controlled, at least in part, by the composition of the solid drug formulation and/or the use of coating substances over one or more surfaces of the solid drug units.

The solid drug units may be coated with one or more suitable bioerodible materials: to slow the onset of drug dissolution and release; to protect the drug against destructive exposure to oxygen or humidity during tablet handling, device assembly, and storage; to lubricate the solid drug units to facilitate device loading; or a combination thereof. Suitable coating materials for these purposes are known in the art.

Similarly, the solid drug units may be mixed/formulated with one or more suitable excipient materials: to alter (e.g., slow or increase) the rate of drug release (e.g., disintegration agents); to protect the drug against destructive exposure to oxygen or humidity during tablet handling, device assembly, and storage; to lubricate the solid drug units to facilitate device loading; to facilitate tableting (e.g., binders) or a combination thereof.

The drug release rate also may be controlled, at least in part, by the composition of the drug formulation. In some embodiments, the solid form of the drug does not include a matrix material, as the inclusion of a matrix material (i.e., dispersing the drug in a degradable or non-degradable matrix material) may reduce the payload efficiency and unnecessarily complicate and/or impede drug release. When impeding drug release is desirable, however, other embodiments can include a matrix material in the drug formulation.

Materials other than the solid drug units may also be added to the housings, specifically the drug reservoir lumens, to alter the drug release. In one embodiment, any space in the drug reservoir lumen that does not contain the drug may be filled with a filling material. This may be done for the purpose of controlling the surface area of drug unit exposed to biological fluid in vivo, and/or for the purpose of adding volume to the overall device where drug payload is not needed but overall device volume is needed, for example, for purposes of enabling or enhancing retention of the device in vivo. Controlling the surface area of drug unit exposed to biological fluid in vivo allows the diffusion rate to be adjusted in certain embodiments.

III. The Drug Formulation and Solid Drug Tablets

Generally, a drug formulation is formed into solid drug units that are loaded into the devices' housings. Each of the solid drug units is a solid, discrete object that substantially retains a selectively imparted shape (at the temperature and pressure conditions to which the delivery device normally will be exposed during assembly, storage, and handling before implantation). The drug units may be in the form of tablets, capsules, pellets, or beads, although other configurations are possible.

The solid drug units can be formed using a stable and scalable manufacturing process. Particularly, the drug tablets are sized and shaped for loading into and efficiently storing the tablets in a housing of a drug delivery device that can be deployed into the bladder or another cavity, lumen, or tissue site in a patient in a minimally invasive manner.

The solid drug units may be made by a direct compression tableting process, a molding process, or other processes known in the pharmaceutical arts. Suitable drug tablet forming methods are described in U.S. Application Publication No. 2010/0330149 (TB 102), which is incorporated herein by reference. The drug formulation also may be loaded into the devices' housings in workable form and may cure therein. For example, in embodiments in which the drug formulation is configured to be melted and solidified, the drug formulation can be melted, injected into the devices' housings in melted form and then solidified. The drug formulation also may be extruded with the devices' housings, may cure within the housings, and subsequently may be cut in spaced positions along the length of the housing to form segments with exposed surface areas of drug.

The solid drug unit includes a drug formulation, which includes a drug content and may include an excipient content. In a preferred embodiment, the drug content includes one or more drugs, or active pharmaceutical ingredients (API), while the excipient content includes one or more pharmaceutically acceptable excipients. The drug formulation can include essentially any therapeutic, prophylactic, or diagnostic agent, such as one that would be useful to deliver locally to a body cavity or lumen or regionally about the body cavity or lumen. The drug formulation may consist only of the API, or one or more excipients may be included. As used herein, the term "drug" with reference to any specific drug described herein includes its alternative forms, such as salt forms, free acid forms, free base forms, and hydrates. The term "excipient" is known in the art, and representative examples of excipients useful in the present drug units may include ingredients such as binders, lubricants, glidants, disintegrants, colors, fillers, diluents, coatings, or preservatives, as well as other non-active ingredients to facilitate manufacturing, stability, dispersibility, wettability, and/or release kinetics of the drug or administering the drug unit. The drug may be small molecule, macromolecule, biologic, or metabolite, among other forms/types of active ingredients.

In order to maximize the amount of drug that can be stored in and released from a given drug delivery device of a selected (small) size, the drug unit preferably comprises a high weight fraction of drug or API, with a reduced or low weight fraction of excipients as are required for solid drug unit manufacturing and device assembly and use considerations. For the purposes of this disclosure, terms such as "weight fraction," "weight percentage," and "percentage by weight" with reference to drug, or API, refers to the drug or API in the form employed, such as in salt form, free acid form, free base form, or hydrate form. For example, a solid drug unit that has 90% by weight of a drug in salt form may include less than 90% by weight of that drug in free base form.

In one embodiment, the solid drug unit is more than 50% by weight drug. In another embodiment, 75% or more of the weight of the solid drug unit is drug, with the remainder of the weight comprising excipients, such as lubricants and binders that facilitate making the solid drug unit. For the purposes of this disclosure, the term "high weight fraction" with reference to the drug or API means that excipients constitute less than 25 wt %, preferably less than 20 wt %, more preferably less than 15 wt %, and even more preferably less than 10 wt % of the solid drug unit. In some cases, the drug content comprises about 75% or more of the weight of the solid drug unit. More particularly, the drug content may comprise about 80% or more of the weight of the drug tablet. For example, the drug content may comprise between about 85% and about 99.9% of the weight of the solid drug unit. In some embodiments, the excipient content can be omitted completely.

In one embodiment, the drug and excipients are selected and the solid drug unit formulated to be water soluble, so that the solid drug units can be solubilized when the device is located within the bladder, to release the solubilized drug.

The individual solid drug units may have essentially any selected shape and dimension that fits within the devices described herein. In one embodiment, the solid drug units are sized and shaped such that the drug reservoir lumens in the housings are substantially filled by a select number of solid drug units. Each solid drug unit may have a cross-sectional shape that substantially corresponds to a cross-sectional shape of the drug reservoir lumen of a particular housing. For example, the drug units may be substantially cylindrical in shape for positioning in a substantially cylindrical drug reservoir lumen. Once loaded, the solid drug units can, in some embodiments, substantially fill the drug reservoir lumens, forming the drug housing portion.

In one embodiment, the solid drug units are shaped to align in a row when the device is in its deployment configuration. For example, each solid drug unit may have a cross-sectional shape that corresponds to the cross-sectional shape of the drug reservoir lumens in the housing, and each solid drug unit may have end face shapes that correspond to the end faces of adjacent solid drug units. The interstices or breaks between solid drug units can accommodate deformation or movement of the device, such as during deployment, while permitting the individual drug units to retain their solid form. Thus, the drug delivery device may be relatively flexible or deformable despite being loaded with a solid drug, as each drug unit may be permitted to move with reference to adjacent drug units.

In embodiments in which the solid drug units are designed for insertion or implantation in a lumen or cavity in the body, such as the bladder, via a drug delivery device, the drug units may be "mini-tablets" that are suitably sized and shaped for insertion through a natural lumen of the body, such as the urethra. For the purpose of this disclosure, the term "mini-tablet" generally indicates a solid drug unit that is substantially cylindrical in shape, having end faces and a side face that is substantially cylindrical. The mini-tablet has a diameter, extending along the end face, in the range of about 1.0 to about 3.2 mm, such as between about 1.5 and about 3.1 mm. The mini-tablet has a length, extending along the side face, in the range of about 1.7 mm to about 4.8 mm, such as between about 2.0 mm and about 4.5 mm. The friability of the tablet may be less than about 2%. Embodiments of solid drug units and systems and methods of making the same are further described below with reference to U.S. Patent Applications incorporated by reference herein.

In one embodiment, the drug formulation is in a solid form. In another embodiment, the drug formulation is in semi-solid form, such as a highly viscous emulsion or suspension; a gel or a paste. As used herein, the solid form includes semi-solid forms unless otherwise indicated.

The drug may be a low solubility drug. As used herein, the term "low solubility" refers to a drug having a solubility from about 0.01 mg/mL to about 10 mg/mL water at 37° C. In other embodiments, the drug is a high solubility drug. As used herein, the term "high solubility" refers to a drug having a solubility above about 10 mg/mL water at 37° C.

In one embodiment, the drug delivery device is used to treat urinary tract cancer, such as bladder cancer and prostate cancer. Drugs that may be used include antiproliferative agents, cytotoxic agents, chemotherapeutic agents, or combinations thereof. Representative examples of drugs which may be suitable for the treatment of urinary tract cancer include Bacillus Calmette Guerin (BCG) vaccine, docetaxel, cisplatin, doxorubicin, valrubicin, gemcitabine, mycobacterial, cell wall-DNA complex (MCC), methotrexate, vinblastine, thiotepa, mitomycin (e.g., mitomycin C), fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may comprise a monoclonal antibody, a TNF inhibitor, an anti-leukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). The drug treatment may be coupled with a conventional radiation or surgical therapy targeted to the cancerous tissue.

In one embodiment, the devices described herein are loaded with an anesthetic agent, analgesic agent, and combinations thereof. The anesthetic agent may be an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocalne, ropivacaine, and trimecaine. Representative examples of aminoesters or ester-class anesthetics include amylocalne, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. These anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The drug also may include other drugs described herein, alone or in combination with a local anesthetic agent.

In certain embodiments, the analgesic agent includes an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents as salicyl alcohol, phenazopyridine hydrochloride, acetaminophen, acetylsalicyclic acid, flufenisal, ibuprofen, indoprofen, indomethacin, and naproxen.

In certain embodiments, the drug delivery device is used to treat inflammatory conditions such as interstitial cystitis, radiation cystitis, painful bladder syndrome, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or combinations thereof. For kidney stones, the drug(s) may be selected to treat pain and/or to promote dissolution of renal stones.

Other non-limiting examples of drugs that may be used in the treatment of IC include nerve growth factor monoclonal antibody (MAB) antagonists, such as Tanezumab, and calcium channel alpha-2-delta modulators, such as PD-299685 or gabepentin. Evidence suggests that the bladder expresses nerve growth factor (NGF) locally, since exogenously delivered NGF into the bladder induces bladder hyperactivity and increases the excitability of dissociated bladder afferent neurons (*Nature Rev Neurosci* 2008; 9:453-66). Accordingly, it would be advantageous to locally deliver a MAB or other agent against NGF using the described delivery devices, significantly reducing the total dose needed for therapeutic efficacy. Evidence also suggests that binding of the alpha-2-delta unit of voltage-sensitive calcium channels, such as with gabapentin, may be effective in the treatment of diseases of neuropathic pain such as fibromyalgia and that there may be common mechanisms between IC and diseases of neuropathic pain (See *Tech Urol.* 2001 March, 7(1):47-49). Accordingly, it would be advantageous to locally deliver a calcium channel alpha-2-delta modulator, such as PD-299685 or gabepentin, using the described delivery devices, minimizing does-related systemic toxicities in the treatment of IC.

Other intravesical cancer treatments include small molecules, such as Apaziquone, adriamycin, AD-32, doxorubicin, doxetaxel, epirubicin, gemcitabine, HTI-286 (hemiasterlin analogue), idarubicin, γ-linolenic acid, mitozantrone, meglumine, and thiotepa; large molecules, such as EGF-dextran, HPC-doxorubicin, IL-12, IFN-a2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridme, HMFG1 Mab+Tc99m; and agents for the management of local toxicity, such as Formalinc (hemorrhagic cystitis).

In one particular embodiment, the drug delivery device is used in association with the placement of a ureteral stent, such as to treat pain, urinary urgency or urinary frequency resulting from ureteral stent placement. Non-limiting examples of specific drugs for such treatment include anti-muscarinics, α-blockers, narcotics, and phenazopyridine, among others.

The drug delivery device can be used, for example, to treat urinary incontinence, frequency, or urgency, including urge incontinence and neurogenic incontinence, as well as trigonitis. Drugs that may be used include anticholinergic agents, antispasmodic agents, anti-muscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), ZD-6169 (Zeneca Co., United Kingdom), and stilonium iodide.

In still another embodiment, the present intravesical drug delivery device is used to treat infections involving the bladder, the prostate, and the urethra. Antibiotics, antibacterial, antifungal, antiprotozoal, antiseptic, antiviral and other anti-infective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the drug delivery device is used to treat fibrosis of a genitourinary site, such as the bladder or uterus. Representative examples of drugs for the treatment of fibroids include pentoxphylline (xanthine analogue), antiTNF, antiTGF agents, GnRH analogues, exogenous progestins, antiprogestins, selective estrogen receptor modulators, danazol and NSAIDs.

The implantable drug delivery device also may be used to treat spastic or flaccid neurogenic bladder. Representative examples of drugs for the treatment of neurogenic bladder include analgesics or anaesthetics, such as lidocaine, bupivacaine, mepivacaine, prilocalne, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal Cord* 42:267-72 (2004).

In one embodiment, the drug is selected from those known for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants); drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamine) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinc agonist, choline ester).

IV. Other Device Features

The devices described herein may include a radio-opaque portion or structure to facilitate detection or viewing (e.g., by X-ray imaging or fluoroscopy) of the device by a medical practitioner as part of the implantation or retrieval procedure. In one embodiment, the housing is constructed of a material that includes a radio-opaque filler material, such as barium sulfate or another radio-opaque material known in the art. Some housings may be made radio-opaque by blending radio-opaque fillers, such as barium sulfate or another suitable material, during the processing of the material from which the housing is formed. The radio-opaque material may be associated with the retention frame in those embodiments that include a retention frame. Ultrasound imaging or fluoroscopy may be used to image the device in vivo.

The housing of the implantable drug delivery device may further include a retrieval feature, such as a string, a loop, or other structure that facilitates removal of the device from the body cavity, for example for removal of a non-resorbable device body following release of the drug formulation from the solid drug units. In one case, the device may be removed from the bladder by engaging the string to pull the device through the urethra. The device may be configured to assume a relatively narrow or linear shape when pulling the device by the retrieval feature into the lumen of a catheter or cystoscope or into the urethra.

V. Methods of Making the Device

An embodiment of a method of making an implantable drug delivery device may include forming a housing, forming a number of solid drug units, loading the solid drug units into the housing, and, if necessary, associating the housing with a retention frame. In some embodiments, the retention frame, if present, may be associated with the housing before loading the solid drug units into the housing.

In some embodiments, forming the housings include forming a flexible body having walls that define one or more drug reservoir lumens and, optionally, a retention frame lumen. For example, the housing may be formed by extruding or molding a polymer, such as silicone. In particular, forming the housing may include integrally forming two tubes or walls that are substantially aligned and adjoined along a longitudinal edge. Alternatively, the two lumens may be separately formed and attached to each other, such as with an adhesive. For embodiments that do not include a retention frame, the housing may be programmed to assume the retention shape. The programming may include heat treating or cross-linking a portion of the material from which the housing is formed. Other methods of forming the housing and imparting the retention shape, if necessary, also may be employed.

Forming a retention frame may include forming an elastic wire or strip from, for example, a superelastic alloy or shape-memory material and "programming" the elastic wire or strip to naturally assume a retention shape. Heat treatment may be used to program the elastic wire or strip to assume a retention shape. For example, the retention frame may be formed by forming the elastic wire or strip into a pretzel shape and heat treating the elastic wire or strip at a temperature over 500° C. for a period over five minutes. In embodiments in which the retention frame comprises a low modulus elastomer, the step of forming the retention frame may comprise forming one or more windings, coils, loops or spirals in the frame so that the retention frame functions as a spring. For example, the retention frame may be formed by extrusion, liquid injection molding, transfer molding, or insert molding, among others.

Associating the housing with a retention frame may comprise inserting a retention frame into a retention frame lumen, if present, associated with the housing. The distal end of the retention frame may be blunted to facilitate driving the retention frame through the retention frame lumen without puncturing the wall of the housing. Associating the housing with the retention frame may further includes filling a retention frame lumen, when present, with a filling material after the retention frame is loaded. The filling material may occupy a portion or all of the remainder of the retention frame lumen not occupied by the retention frame. Associating the housing with the retention frame portion may comprise integrally forming the two portions together, such as by overmolding the housing about the retention frame.

The monolithic housing or modular housing units may be made by a molding or extrusion process. The molded or extruded structures may be further processed into the complete housing by one or more of cutting, drilling, or mechanically punching to form the individual drug reservoir lumens and/or modular housing unit. Alternatively, drug reservoir lumens or through-holes may be molded into the structure. Components may also be assembled or connected together with adhesives, fasteners, and/or strung together with the retention frame.

The solid drug units may be loaded into the drug delivery device by any suitable means, as described above with reference to FIGS. 11-22. Other solid drug unit loading methods can be used.

Some steps or sub-steps of the method of making an implantable drug delivery device may be performed in other orders or simultaneously. For example, the retention frame may be associated with the housing either before or after the drug units are loaded into the device body.

VI. Methods for Drug Delivery

The devices and methods disclosed herein may be adapted for use in humans, whether male or female, adult or child, or for use in animals, such as for veterinary or livestock applications. Accordingly, the term "patient" may refer to a human or other mammalian subject.

The device may be implanted non-surgically and may deliver drug for several days, weeks, months, or more after the implantation procedure has ended. For example, the device may be deployed through a deployment instrument, such as a catheter or cystoscope, positioned in a natural lumen of the body, such as the urethra, into a body cavity, such as the bladder. The deployment instrument typically is removed from the body lumen while the drug delivery device remains in the bladder or other body cavity for a prescribed treatment period.

The device, in some embodiments, may be deployed into the bladder of a patient in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In one example, the device is implanted by passing the drug delivery device through a deployment instrument and releasing the device from the deployment instrument into the body. In cases in which the device is deployed into a body cavity such as the bladder, the device assumes a retention shape, such as an expanded or higher profile shape, once the device emerges from the deployment instrument into the cavity. The deployment instrument may be any suitable lumen device, such as a catheter, e.g., a urethral catheter, or cystoscope. These terms are used interchangeably herein, unless otherwise expressly indicated. The deployment instrument may be a commercially available device or a device specially adapted for the present drug delivery devices.

The drug delivery device may be passed through the deployment instrument, driven by a stylet or flow of lubricant or other fluid, for example, until the drug delivery device exits a lumen of the instrument as passes into the bladder. Thus, the device may be implanted into the bladder of a male or female human patient in need of treatment, either adult or child.

Once deployed in vivo, the device subsequently may release one or more drugs for the treatment of one or more conditions, locally to one or more tissues at the deployment site and/or regionally to other tissues distal from the deployment site. The release may be controlled and may release the drug in an effective amount over an extended period. Thereafter, the device may be removed, resorbed, excreted, or some combination thereof. In certain embodiments, the device resides in the bladder releasing the drug over a predetermined period, such as two weeks, three weeks, four weeks, a month, or more.

Once implanted, the device may provide extended, continuous, intermittent, or periodic release of a desired quantity of drug over a desired, predetermined period. In embodiments, the device can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated.

In certain embodiments, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. For example, the drug may be solubilized upon contact with urine in cases in which the device is implanted in the bladder.

The device may be used to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may release drug locally to the bladder and regionally to other sites near the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including the kidneys, urethra, ureters, penis, testes, seminal vesicles, vas deferens, ejaculatory ducts, prostate, vagina, uterus, ovaries, or fallopian tubes, among others or combinations thereof. For example, the drug delivery device may be used in the treatment of kidney stones or fibrosis, erectile dysfunction, among other diseases, disorders, and conditions.

In one embodiment, the drug delivery device is implanted into a bladder to locally deliver an anesthetic agent for management of pain arising from any source, such as a disease or disorder in genitourinary tissues, or pain stemming from any bladder procedure, such as surgery, catheterization, ablation, medical device implantation, or stone or foreign object removal, among others. For example, an anesthetic agent can be released into the bladder for regional delivery to nearby sites to manage nearby pain arising from any source, such as post-operative pain associated with the passage of a medical device into or through a ureter or other post-operative pain in sites apart from the bladder.

In one embodiment, a device having a payload of mitomycin C may be delivered to the bladder, and the mitomycin C may be continuously released from the device over an extended period. The drug payload, in this embodiment, is in a solid form, to reduce the size of the device and thereby to reduce bladder irritation and patient discomfort.

In one embodiment, the device may have two payloads of drug that are released at different times. The first payload may be adapted for relatively quick release, while the second payload may be adapted for more continuous release.

Subsequently, the device may be retrieved from the body, such as in cases in which the device is non-resorbable or otherwise needs to be removed. Retrieval devices for this purpose are known in the art or can be specially produced. The device also may be completely or partially bioerodible, resorbable, or biodegradable, such that retrieval is unnecessary, as either the entire device is resorbed or the device sufficiently degrades for expulsion, for example, from the bladder during urination. The device may not be retrieved or resorbed until some of the drug, or preferably most or all of the drug, has been released. If needed, a new drug-loaded device may subsequently be implanted, during the same procedure as the retrieval or at a later time.

The present invention may be further understood with reference to the following non-limiting examples.

EXAMPLE 1

Diffusion of Mitomycin C from Different Device Designs

A study was performed to determine the feasibility of delivering mitomycin C ("MMC"), a low aqueous solubility drug, from various housing structures. Eight total devices—two devices of four different configurations—were formed from 2.65 mm ID ("600" tubing) silicone tubes, and loaded with pressed tablets of MMC tablets for a total payload of about 60 mg.

The four configurations were (1) a device having a single open end, presenting a single face of the MMC tablet, (2) a device having two opposed open ends, presenting two faces of the MMC tablets, (3) a device having two opposed open ends and a slit in the tubing between two MMC tablets, thereby effectively presenting four faces of the MMC tablets, and (4) and an uncontained MMC tablet (i.e. no housing), exposing the entire outer surface of the tablet. Two of each configuration was tested.

Each of the four configurations was separately placed into 100 mL of deionized water at 37° C. The first three configurations of drug/device provided a constant surface area of the solid drug for contact with the water over the test period. In contrast, with the fourth configuration—the uncontained drug tablets—the surface area of solid drug exposed to water changed over time as the drug at the surface dissolved. Dissolution/release of the MMC was periodically measured by removing aliquots of the water and analyzing for MMC using HPLC directly after each time point.

Figure 40:
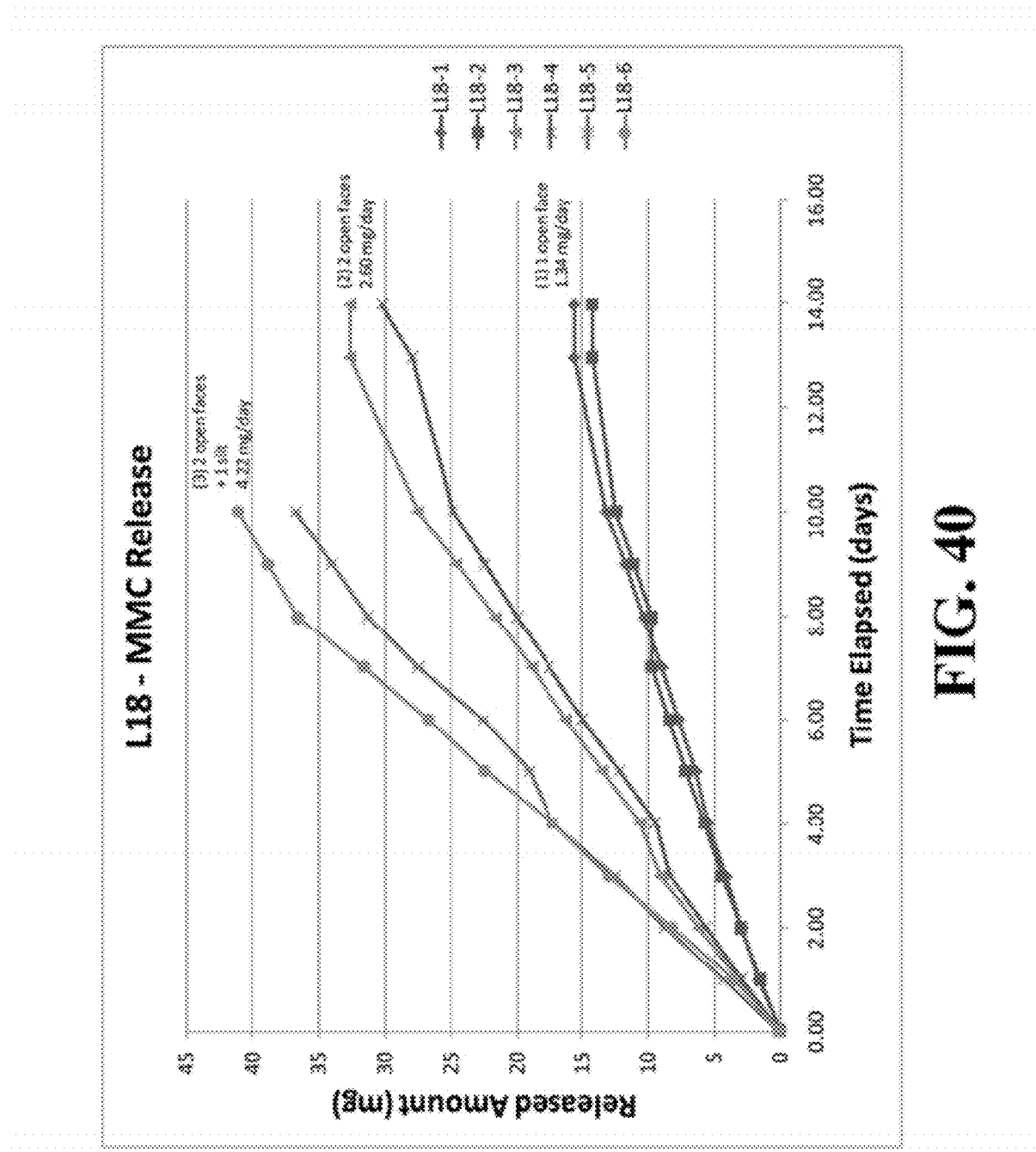
FIG. 40 is a graphical depiction of the amount of drug released from a series of test devices.

The release rate over 7 days was calculated. As shown in FIG. 40, the release profile data demonstrated that it is feasible to deliver drug via dissolution and diffusion from open areas in the silicone housing structures and that the release rate can be increased by increasing the surface area of the solid drug form that is exposed to the fluid environment, e.g., the aqueous solution, in which the drug-loaded device is deployed.

Figure 41:
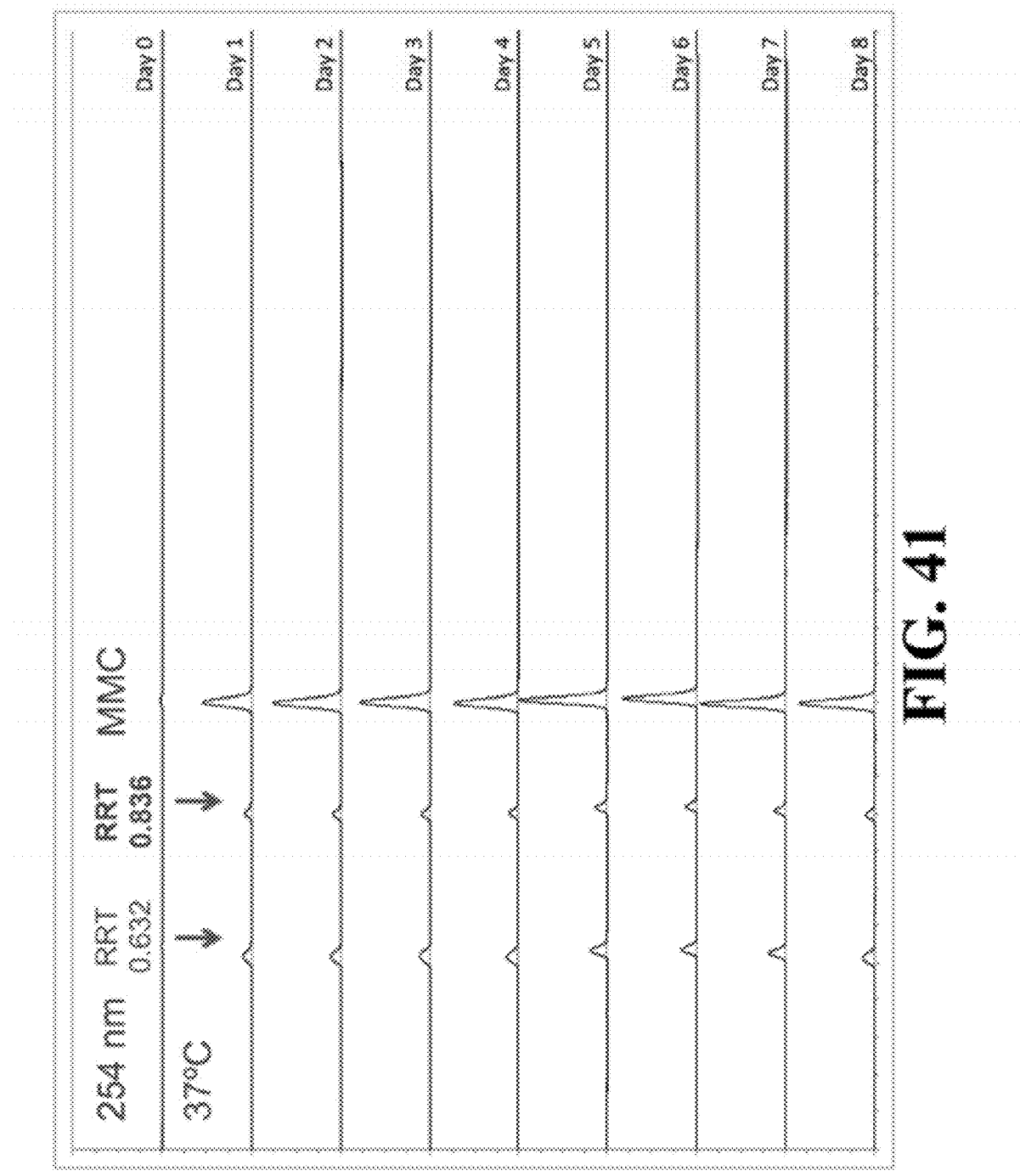
FIG. 41 is a depiction of the chromatograms collected during a test of several devices.

FIG. 41 shows the chromatograms for each of days 0-8 for configuration 3. The relatively constant level of MMC can be observed. The related compounds (RRT 0.632 and RT 0.836) are believed to be degradation products of the MMC. It is noted, however, that the degradation products do not increase over time, which suggests that the MMC degradation does not occur while housed in the device but primarily or entirely following dissolution and release.

EXAMPLE 2

In Vitro Release of Mitomycin C from Housing Module

Housing device modules loaded with tablets of mitomycin C (MMC) were made and a in vitro release of the MMC was observed.

Figure 42B:
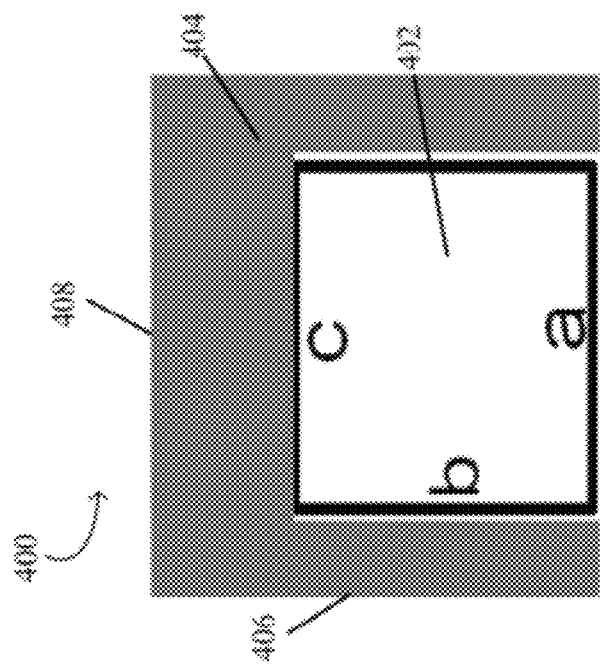
FIGS. 42a and 42b illustrate a tablet made of 100% mitomycin C (MMC) and a housing module containing the tablet, which was used in an in vitro release rate experiment.
Figure 42A:
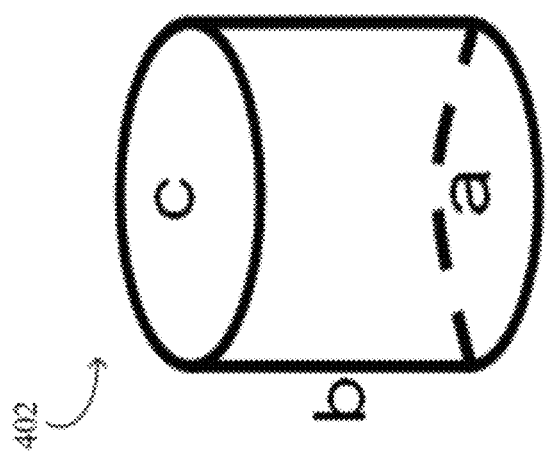

Tablets were made using Carver Press from 100% mitomycin C powder. The diameter of the tablets was either 2.1 mm or 2.6 mm with the height of 2 mm. The mass of the tablet was approximately 10 mg for 2.1 mm diameter tablet and 16 mg for 2.6 mm diameter tablet. The MMC tablet 402 is shown in FIG. 42a.

Housing modules were made from segments of silicone tube and silicone adhesive. FIG. 42b shows assembled device module 400, wherein MMC tablet 402 is shown loaded into housing module 404. The surface 'b' of tablet 402 was surrounded by silicone tube 406 and the surface 'c' was in contact with silicone adhesive 408.

Figure 43:
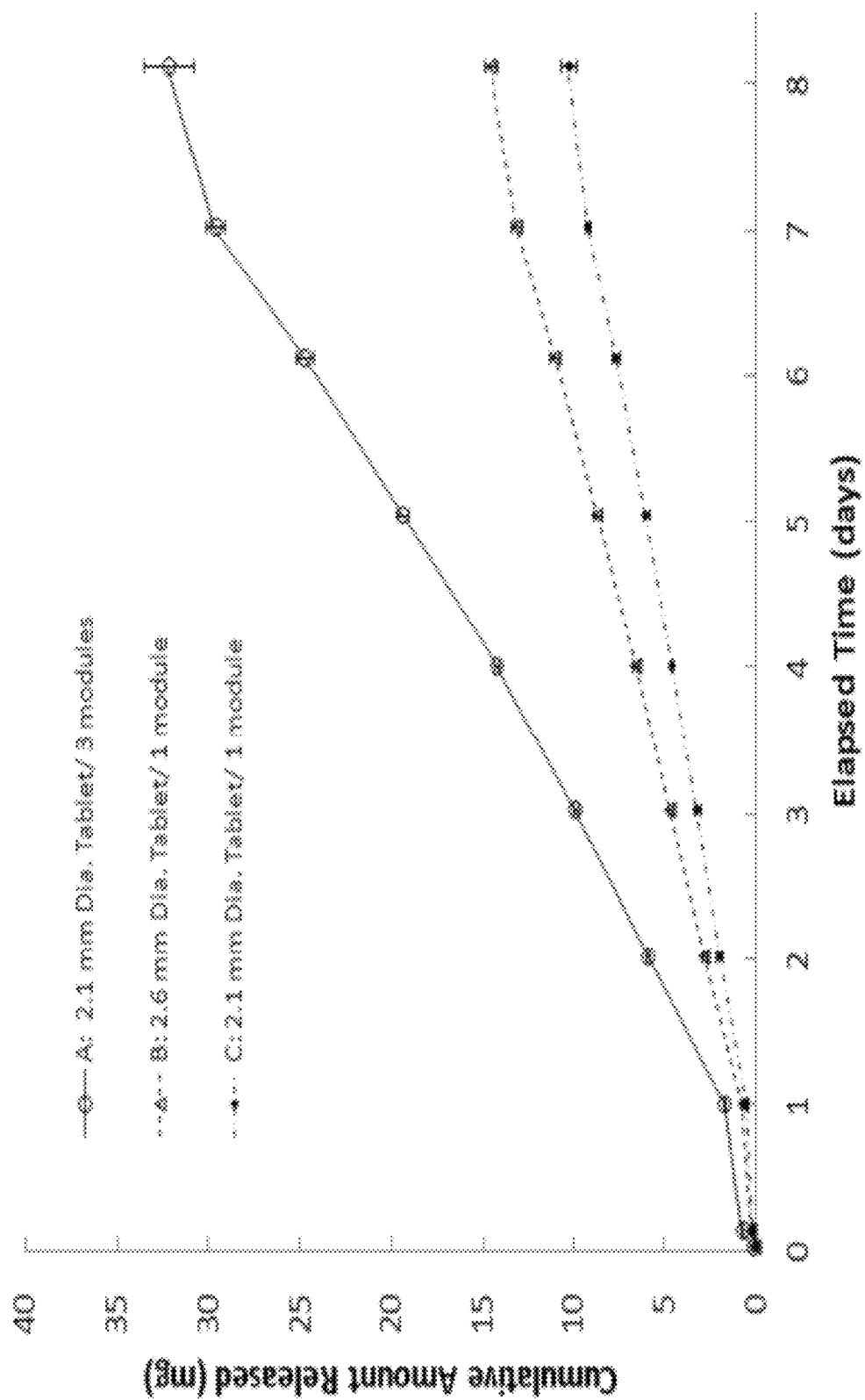
FIG. 43 is a graph showing cumulative release of MMC in vitro over an extended period, comparing device module designs having varying surface areas of 100% MMC tablets exposed to a release media.

The surface 'a' of the MMC tablet 402 was exposed to a release medium of deionized water for a test period of 8 days. Specifically, the housing module 400 was submerged in 20 mL deionized water at 37° C., with the release medium being entirely replenished daily during the test period. The cumulative release of MMC was measure over the test period. In vitro release data is shown in FIG. 43 (n=3; the error bars indicate S.D. around the mean.) (Some error bars are not shown, i.e., when they are smaller than the symbols.).

It was observed that the erosion surface propagated from the surface 'a' to the surface 'c' and the near zero order release was achieved until the tablet was all eroded. In 'A', three modules were used while one was used in 'C'. The data shows that the release rate was determined by the total exposed area, or the surface 'a' in FIG. 42b.

EXAMPLE 3

In Vitro Release of Mitomycin C from Housing Module

Figure 44:
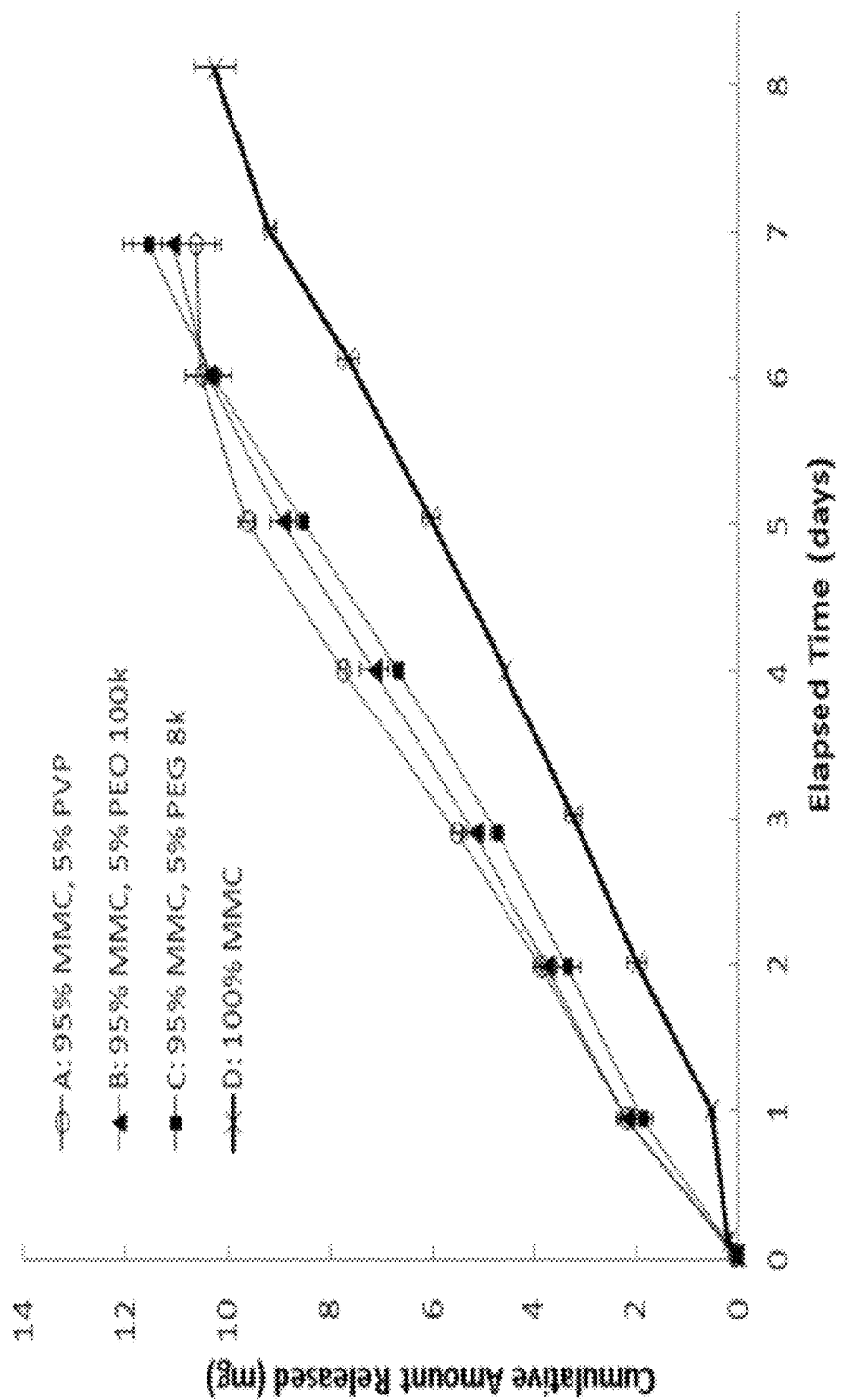
FIG. 44 is a graph showing cumulative release of MMC in vitro over an extended period, comparing device modules loaded with tablets of different MMC/excipients formulations.

The experiment described in Example 2 was repeated with modifications to the MMC tablet formulation, to observe the effect of including excipients. The same configuration and experiment method as 'C' in FIG. 43 was used. 2.1 mm diameter tablets with a height of 2 mm were made by adding 5% (w/w) PVP (Plasdone K-29/32), PEO 100K, or PEG 8K to 95% mitomycin C powder and then pressing the mixture to form tablets, each having a mass of approximately 10 mg. As shown in FIG. 44, an increased release rate was observed with the addition of these excipients (n=3; the error bars indicate S.D. around the mean) (Some error bars are not shown, i.e., when they are smaller than the symbols.).

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. An implantable drug delivery device comprising:
    a drug housing portion which comprises
        at least one solid drug unit comprising a drug, and
        at least one housing having at least one defined opening, wherein the at least one solid drug unit is located within the defined opening such that the housing encases a first portion of the surface of the at least one solid drug unit and exposes a second portion of the surface of the at least one solid drug unit,
    wherein the device is elastically deformable between a relatively straightened shape suited for insertion through a lumen into a body cavity of a patient and a retention shape suited to retain the device within the body cavity, and
    wherein release of the drug from the device is controlled by erosion of the exposed second portion of the surface of the at least one solid drug unit.

2. The device of claim 1, wherein the at least one solid drug unit is a tablet which comprise a low solubility drug.

3. The device of claim 1, wherein the drug comprises gemcitabine, docetaxel, carboplatin, cisplatin, trospium, tolterodine, mitomycin C, or a combination thereof.

4. The device of claim 1, wherein the rate of the release of the drug from the drug delivery device is zero order over at least 24 hours.

5. An implantable drug delivery device comprising:
    a drug housing portion which comprises
        at least two solid drug units, and
        at least one housing encasing a first portion of the surface of each solid drug unit, and having at least two defined openings that expose a second portion of the surface of each solid drug unit,
    wherein the device is elastically deformable between a relatively straightened shape suited for insertion through a lumen into a body cavity of a patient and a retention shape suited to retain the device within the body cavity, and
    wherein release of the drug from the device is controlled by erosion of the exposed second portion of the surface of the solid drug units,
    wherein the at least one housing is configured to expose a constant surface area of the at least two solid drug units at the at least two defined openings as the at least two solid drug units are dissolved at the exposed surface area.

6. The drug delivery device of claim 5, wherein the at least one housing comprises at least three defined openings so that a third portion of the surface of at least one solid drug unit is exposed.

7. The drug delivery device of claim 5, wherein the at least one housing comprises at least four defined openings so that a third portion of the surface of each solid drug unit is exposed.

8. The drug delivery device of claim 5, wherein the solid drug unit comprises a low solubility drug.

9. The drug delivery device of claim 5, wherein the at least one housing comprises a flexible elongated monolithic structure having a longitudinal axis and a plurality of separate drug reservoir lumens oriented substantially perpendicularly to the longitudinal axis.

10. The drug delivery device of claim 9, wherein the at least one housing further comprises a retention frame lumen oriented substantially parallel to the longitudinal axis.

11. The drug delivery device of claim 5, wherein the at least one housing comprises two or more modular housing units.

12. The drug delivery device of claim 11, wherein the two or more modular housing units each comprise:
    (i) a drug reservoir lumen housing at least one of the solid drug units, and
    (ii) at least one retention frame lumen, the plurality of modular housing units having a shared retention frame extending through the retention frame lumens.

13. The drug delivery device of claim 12, wherein the drug reservoir lumen has two opposed openings which expose correspondingly opposed end surfaces of the at least one solid drug units housed therein.

14. The drug delivery device of claim 12, wherein the drug reservoir lumen is oriented substantially parallel to the retention frame lumen.

15. The drug delivery device of claim 12, wherein the drug reservoir lumen is oriented substantially perpendicular to the retention frame lumen.

16. The drug delivery device of claim 5, further comprising a retention frame.

17. The drug delivery device of claim 16, wherein the retention frame comprises a superelastic alloy wire or strip.

18. The drug delivery device of claim 5, wherein the at least two solid drug units comprise gemcitabine, docetaxel, carboplatin, cisplatin, trospium, tolterodine, mitomycin C, or a combination thereof.

* * * * *